(12) United States Patent
Hansen

(10) Patent No.: US 9,883,332 B2
(45) Date of Patent: *Jan. 30, 2018

(54) SYSTEM AND METHOD OF AN EVENT TIMING SYSTEM HAVING INTEGRATED GEODETIC TIMING POINTS

(71) Applicant: Innovative Timing Systems, LLC, St. Louis, MO (US)

(72) Inventor: Kurt S. Hansen, Chesterfield, MO (US)

(73) Assignee: Innovative Timing Systems, LLC, St. Louis, MO (US)

( * ) Notice: Subject to any disclaimer, the term of this patent is extended or adjusted under 35 U.S.C. 154(b) by 128 days.

This patent is subject to a terminal disclaimer.

(21) Appl. No.: 14/776,697

(22) PCT Filed: Mar. 17, 2014

(86) PCT No.: PCT/US2014/030537
§ 371 (c)(1),
(2) Date: Sep. 14, 2015

(87) PCT Pub. No.: WO2014/145728
PCT Pub. Date: Sep. 18, 2014

(65) Prior Publication Data
US 2016/0029158 A1    Jan. 28, 2016

Related U.S. Application Data

(63) Continuation-in-part of application No. 13/980,545, filed as application No. PCT/US2012/022132 on Jan.
(Continued)

(51) Int. Cl.
*H04W 4/02* (2009.01)
*G07C 1/24* (2006.01)
(Continued)

(52) U.S. Cl.
CPC .......... *H04W 4/02* (2013.01); *G06F 19/3418* (2013.01); *G06F 19/3481* (2013.01); *G07C 1/24* (2013.01);
(Continued)

(58) Field of Classification Search
CPC .. H04W 4/02; G07C 1/24; G07C 1/22; G07C 9/00103; G07C 9/00111; G07C 3/08;
(Continued)

(56) References Cited

U.S. PATENT DOCUMENTS 4,142,680 A    3/1979    Oswald et al.
4,505,595 A    3/1985    Rose et al.
(Continued)

FOREIGN PATENT DOCUMENTS

DE    102005026559 A1    12/2006
EP       1548674 A1     6/2005
(Continued)

OTHER PUBLICATIONS

U.S. Appl. No. 14/775,478, filed Sep. 11, 2015.
(Continued)

*Primary Examiner* — Lester Kincaid
*Assistant Examiner* — Gary Lafontant
(74) *Attorney, Agent, or Firm* — Senniger Powers LLP

(57) ABSTRACT

A system and method for determining a route or waypoints along a route to be or being traveled by a participant, the system including a location device associated with the participant having a location data receiver for receiving location data from a location providing source, and a wireless communication interface, the location detection device receiving location information from the location providing source, time stamping each received location information, and transmitting location data associated with the location device over the wireless interface; a location detection
(Continued)

device in at least periodic wireless communication with the location device for receiving the transmitted location data, and transmitting the received location data; and an event/timing system receiving the transmitted location data, and determining a route or waypoints along a route to be or being traveled by a participant that will be tracked.

27 Claims, 13 Drawing Sheets

Related U.S. Application Data 20, 2012, now Pat. No. 9,489,552, application No. 14/776,697, which is a continuation-in-part of application No. 13/582,148, filed as application No. PCT/US2011/026717 on Mar. 1, 2011, now Pat. No. 9,504,896, application No. 14/776,697, which is a continuation-in-part of application No. 14/793,370, filed on Jul. 7, 2015, which is a continuation of application No. 13/194,880, filed on Jul. 29, 2011, now Pat. No. 9,076,278, application No. 14/776,697, which is a continuation-in-part of application No. 14/374,757, filed as application No. PCT/US2013/023167 on Jan. 25, 2013, application No. 14/776,697, which is a continuation-in-part of application No. 13/980,539, filed as application No. PCT/US2012/022125 on Jan. 20, 2012, now Pat. No. 9,375,627, application No. 14/776,697, which is a continuation-in-part of application No. 14/374,753, filed as application No. PCT/US2013/023274 on Jan. 25, 2013, now Pat. No. 9,495,568.

(60) Provisional application No. 61/801,012, filed on Mar. 15, 2013, provisional application No. 61/434,782, filed on Jan. 20, 2011, provisional application No. 61/369,013, filed on Jul. 29, 2010, provisional application No. 61/309,259, filed on Mar. 1, 2010, provisional application No. 61/590,782, filed on Jan. 25, 2012, provisional application No. 61/434,769, filed on Jan. 20, 2011, provisional application No. 61/590,667, filed on Jan. 25, 2012.

(51) Int. Cl.
  *G06F 19/00* (2011.01)
  *H04W 4/00* (2009.01)
  *G06K 17/00* (2006.01)
  *A61B 5/11* (2006.01)

(52) U.S. Cl.
  CPC ............ *H04W 4/008* (2013.01); *A61B 5/1113* (2013.01); *A61B 2503/10* (2013.01); *G06K 2017/0045* (2013.01)

(58) Field of Classification Search
  CPC .............. G07C 5/008; G06Q 30/0261; G06Q 30/0267; G06Q 10/0833; G06Q 10/047; H04N 7/188; H04N 1/00164; H04N 1/00342; G08B 13/19608
  USPC ...................................................... 455/456.1
  See application file for complete search history.

(56) References Cited

U.S. PATENT DOCUMENTS

| | | |
|---|---|---|
| 4,588,881 A | 5/1986 | Pejas et al. |
| 4,812,845 A | 3/1989 | Yamada et al. |
| 4,918,630 A | 4/1990 | Plouff et al. |
| 5,091,895 A | 2/1992 | Chatwin et al. |
| 5,140,307 A | 8/1992 | Rebetez et al. |
| 5,436,611 A | 7/1995 | Arlinghaus, Jr. |
| 5,493,805 A | 2/1996 | Penuela et al. |
| 5,511,045 A | 4/1996 | Sasaki et al. |
| 5,604,485 A | 2/1997 | Lauro et al. |
| 5,696,481 A | 12/1997 | Pejas et al. |
| 5,812,049 A | 9/1998 | Uzi |
| 5,821,902 A | 10/1998 | Keen |
| 5,883,582 A | 3/1999 | Bowers et al. |
| 5,973,598 A | 10/1999 | Beigel |
| 6,008,773 A | 12/1999 | Matsuoka et al. |
| 6,100,804 A | 8/2000 | Brady et al. |
| 6,204,813 B1 | 3/2001 | Wadell et al. |
| 6,278,413 B1 | 8/2001 | Hugh et al. |
| 6,340,932 B1 | 1/2002 | Rodgers et al. |
| 6,369,697 B1 | 4/2002 | Poole |
| 6,466,178 B1 | 10/2002 | Muterspaugh |
| 6,496,806 B1 | 12/2002 | Horwitz et al. |
| 6,512,478 B1 | 1/2003 | Chien |
| 6,570,487 B1 | 5/2003 | Steeves |
| 6,577,238 B1 | 6/2003 | Whitesmith et al. |
| 6,696,954 B2 | 2/2004 | Chung |
| 6,703,935 B1 | 3/2004 | Chung et al. |
| 6,710,713 B1 | 3/2004 | Russo |
| 6,720,930 B2 | 4/2004 | Johnson et al. |
| 6,812,824 B1 | 11/2004 | Goldinger et al. |
| 6,839,027 B2 | 1/2005 | Krumm et al. |
| 6,888,459 B2 | 5/2005 | Stilp |
| 6,888,502 B2 | 5/2005 | Beigel et al. |
| 6,952,157 B1 | 10/2005 | Stewart et al. |
| 6,963,270 B1 | 11/2005 | Gallagher et al. |
| 6,989,750 B2 | 1/2006 | Shanks et al. |
| 6,995,655 B2 | 2/2006 | Ertin et al. |
| 7,009,562 B2 | 3/2006 | Jenabi |
| 7,019,639 B2 | 3/2006 | Stilp |
| 7,057,511 B2 | 6/2006 | Shanks et al. |
| 7,057,975 B2 | 6/2006 | Stobbe |
| 7,339,478 B2 | 3/2008 | Le |
| 7,508,739 B2 | 3/2009 | Paes |
| 7,589,616 B2 | 9/2009 | Klatsmanyi et al. |
| 7,605,685 B2 | 10/2009 | Stewart et al. |
| 7,605,689 B2 | 10/2009 | Hein et al. |
| 8,085,136 B2 | 12/2011 | Stewart et al. |
| 8,179,233 B2 | 5/2012 | Kia |
| 8,332,281 B2 | 12/2012 | Smith et al. |
| 8,442,922 B2 | 5/2013 | Martin |
| 9,489,552 B2 * | 11/2016 | Hansen .................. G06Q 50/10 |
| 2001/0030625 A1 | 10/2001 | Doles et al. |
| 2001/0040895 A1 | 11/2001 | Templin |
| 2002/0008622 A1 | 1/2002 | Weston et al. |
| 2002/0008624 A1 | 1/2002 | Paek |
| 2002/0044057 A1 | 4/2002 | Zirbes |
| 2002/0044096 A1 | 4/2002 | Chung |
| 2003/0014678 A1 | 1/2003 | Ozcetin et al. |
| 2003/0073518 A1 | 4/2003 | Marty et al. |
| 2003/0163287 A1 | 8/2003 | Vock et al. |
| 2003/0189484 A1 | 10/2003 | Rust et al. |
| 2004/0006445 A1 | 1/2004 | Paek |
| 2005/0093976 A1 | 5/2005 | Valleriano et al. |
| 2005/0099269 A1 | 5/2005 | Diorio et al. |
| 2005/0138798 A1 | 6/2005 | Sakama et al. |
| 2006/0097847 A1 | 5/2006 | Bervoets et al. |
| 2006/0097874 A1 | 5/2006 | Salesky et al. |
| 2006/0103536 A1 | 5/2006 | Kwak et al. |
| 2006/0158313 A1 | 7/2006 | Satou |
| 2006/0176216 A1 | 8/2006 | Hipskind |
| 2006/0180647 A1 | 8/2006 | Hansen |
| 2007/0076528 A1 | 4/2007 | Kirby |
| 2007/0097969 A1 | 5/2007 | Regnier |
| 2007/0182567 A1 | 8/2007 | Stewart et al. |
| 2007/0252770 A1 | 11/2007 | Kai et al. |
| 2007/0254619 A1 | 11/2007 | Salomone et al. |
| 2007/0262871 A1 | 11/2007 | Yamagajo et al. |
| 2007/0272011 A1 | 11/2007 | Chapa, Jr. et al. |
| 2008/0018479 A1 | 1/2008 | Hashimoto et al. |
| 2008/0021676 A1 | 1/2008 | Vock et al. |
| 2008/0045806 A1 | 2/2008 | Keppler |
| 2008/0111695 A1 | 5/2008 | Yamagajo et al. |

(56) References Cited

U.S. PATENT DOCUMENTS

| | | |
|---|---|---|
| 2008/0139263 A1 | 6/2008 | He et al. |
| 2008/0143620 A1 | 6/2008 | Khatri |
| 2008/0246615 A1 | 10/2008 | Duron et al. |
| 2008/0246616 A1 | 10/2008 | Sakama et al. |
| 2008/0249867 A1 | 10/2008 | Angell et al. |
| 2008/0284654 A1 | 11/2008 | Burnside et al. |
| 2008/0316032 A1 | 12/2008 | Kia |
| 2009/0015377 A1 | 1/2009 | Fogg et al. |
| 2009/0141138 A1 | 6/2009 | DeAngelis |
| 2009/0184806 A1 | 7/2009 | Kia |
| 2009/0231198 A1 | 9/2009 | Walsh et al. |
| 2009/0284368 A1 | 11/2009 | Case, Jr. |
| 2009/0284375 A1 | 11/2009 | Kuo et al. |
| 2010/0019897 A1 | 1/2010 | Stewart et al. |
| 2010/0050253 A1 | 2/2010 | Baughman et al. |
| 2010/0051701 A1 | 3/2010 | Ogata et al. |
| 2010/0088023 A1 | 4/2010 | Werner |
| 2010/0185398 A1 | 7/2010 | Berns et al. |
| 2010/0271263 A1 | 10/2010 | Moshfeghi |
| 2010/0283630 A1 | 11/2010 | Alonso |
| 2010/0295943 A1 | 11/2010 | Cha et al. |
| 2010/0302910 A1 | 12/2010 | Howell |
| 2010/0308965 A1 | 12/2010 | Weitzhandler et al. |
| 2011/0018689 A1 | 1/2011 | McAllister et al. |
| 2011/0054792 A1 | 3/2011 | McClellan |
| 2011/0055045 A1 | 3/2011 | Smith et al. |
| 2011/0124469 A1* | 5/2011 | Uhlir .................... A63F 13/216 482/8 |
| 2011/0141221 A1 | 6/2011 | Satterlee et al. |
| 2011/0227748 A1 | 9/2011 | Schaible et al. |
| 2011/0251972 A1 | 10/2011 | Martin |
| 2011/0298583 A1 | 12/2011 | Libby et al. |
| 2012/0025944 A1 | 2/2012 | Hansen |
| 2012/0081531 A1 | 4/2012 | DeAngelis et al. |
| 2012/0115557 A1 | 5/2012 | Kia |
| 2012/0230240 A1 | 9/2012 | Nebat et al. |
| 2012/0299725 A1 | 11/2012 | Boyd et al. |
| 2012/0319822 A1 | 12/2012 | Hansen |
| 2013/0040660 A1 | 2/2013 | Fisher et al. |
| 2014/0052279 A1 | 2/2014 | Van Rens |

FOREIGN PATENT DOCUMENTS

| | | |
|---|---|---|
| EP | 2009595 A | 12/2008 |
| EP | 2033146 B1 | 8/2011 |
| EP | 2009595 B1 | 11/2012 |
| JP | 2000271259 A | 10/2000 |
| JP | 2002281492 A | 9/2002 |
| JP | 2003-327331 A | 11/2003 |
| JP | 2006-004065 A | 1/2006 |
| JP | 2006-053655 A | 2/2006 |
| JP | 2006280670 A | 10/2006 |
| JP | 2008-276353 A | 11/2006 |
| JP | 2007228195 A | 9/2007 |
| JP | 2008-299535 A | 12/2008 |
| JP | 4394600 A | 10/2009 |
| JP | 2010-088886 A | 4/2010 |
| JP | 2010-202998 A | 9/2010 |
| JP | 2011-002958 A | 1/2011 |
| KR | 10-2002-0008234 A | 1/2002 |
| KR | 10-2002-0065429 A | 8/2002 |
| KR | 10-0438359 B1 | 7/2004 |
| KR | 10-2006-0078335 A | 7/2006 |
| KR | 10-2007-0092982 A | 9/2007 |
| KR | 10-2008-0090269 A | 10/2008 |
| KR | 10-2010-0100500 A | 9/2010 |
| KR | 10-2010-0119271 A | 11/2010 |
| WO | 2009050662 A1 | 4/2009 |
| WO | 2009073742 A1 | 6/2009 |
| WO | 2010138882 A1 | 12/2010 |
| WO | 2011109419 A2 | 9/2011 |

OTHER PUBLICATIONS

U.S. Appl. No. 13/980,675, filed Sep. 11, 2013.
U.S. Appl. No. 13/582,148, filed Aug. 31, 2012.
U.S. Appl. No. 14/793,370, filed Jul. 7, 2015.
U.S. Appl. No. 13/946,238, filed Jul. 19, 2013.
U.S. Appl. No. 14/776,584, filed Sep. 14, 2015.
U.S. Appl. No. 13/980,539, filed Jul. 18, 2013.
Electronic Product Code (EPC) Tag Data Standards Version 1.1 Rev. 1.24; EPC Global, Inc. Apr. 1, 2004.
Integration of RFID and Cellular Technologies, UCLA, WINMEC 2004; Karali, Sep. 2004.
Alien Debuts Gen 2 Interrogator, RFID Journal; O'Connor, Aug. 4, 2005.
Antenna Design for UHF RFID Tags: A Review and a Practical Application, IEEE Transactions on Antennas and Propagation, vol. 53, No. 12; Rao and Nikitin, Dec. 2005.
Electronic Product Code (EPC) Radio-Frequency Indentity Protocols Class-1 Generation-2 UHF FRID Protocol for Communications at 860 MHz-960 Mhz, Version 1.0.9; EPC Global, Inc., Jan. 2005.
Electronic Product Code (EPC) Generation 1 Tag Data Standards Version 1.1 Rev.1.27; EPC Global, Inc., May 10, 2005.
UHF Gen 2 System Overview, TI-RFID; Texas Instruments, Mar. 2005.
Trolleyponder/Ecotag RFID Newsletter, No. 51; Trolley Scan Pty Ltd, Jan. 5, 2006.
Tests on Timing Module for Sports Timing; Trolley Scan Pty, Jun. 2004.
New for 2005—Best Racing now uses DAG chip timing; DAG 2005.
Intermec RFID System Manual; Intermec 2005.
RFID Primer; Alien Technology, 2004.
DAG System Instructions, Version 4; Pygma Lyon (DAG), Jul. 9, 2004.
DAG System Instructions—DAG Triathlon, Version 5; Pygma Lyon (DAG) Jul. 23, 2004.
DAG System—Badgeur V2 Sport Version Datasheet; Pygma Lyon (DAG), Jul. 19, 2004.
Annex 1: Utilization of the Dag Badger System; Pygma Lyon (DAG).
Alien RFID Academy Training Manual; Alien Technology, Sep. 22, 2004.
Alien Advanced RFID Academy; Alien Technology, Mar. 16, 2005.
Reader Interface Guide, V2.1.0; Alien Technology, 2004.
Mobile RFID Reader with Database Wireless Synchronization, S. Sandoval-Reyes, et al, 2nd ICEEE and CIE2005, Mexico City, Sep. 7-9, 2005.
Tag Programming Guide, Nanoscanner Reader v01.02.01, Alien Technology, 2003.
Mitigating the Reader Collision Problem in RFID Networks with Mobile Readers, Shailesh M. Birair and Sridhar Iyer, Indian Institute of Technology, Mumbai, India, 400 076, IEEE, 2005.
Trolley Scan Timing Module Brochure Jun. 2004; Trolley Scan Pty Ltd, Jun. 30, 2004.
The Practical Feasibility of Using RFID in a Metal Environment, IEEE, Arora IIT, Mar. 11, 2007.
Omni-ID The Technology of On-Metal RFID, Omni-ID White Paper, Sep. 2009.
PCT Search Report, PCT US 2014-030537, dated Aug. 28, 2014.

* cited by examiner

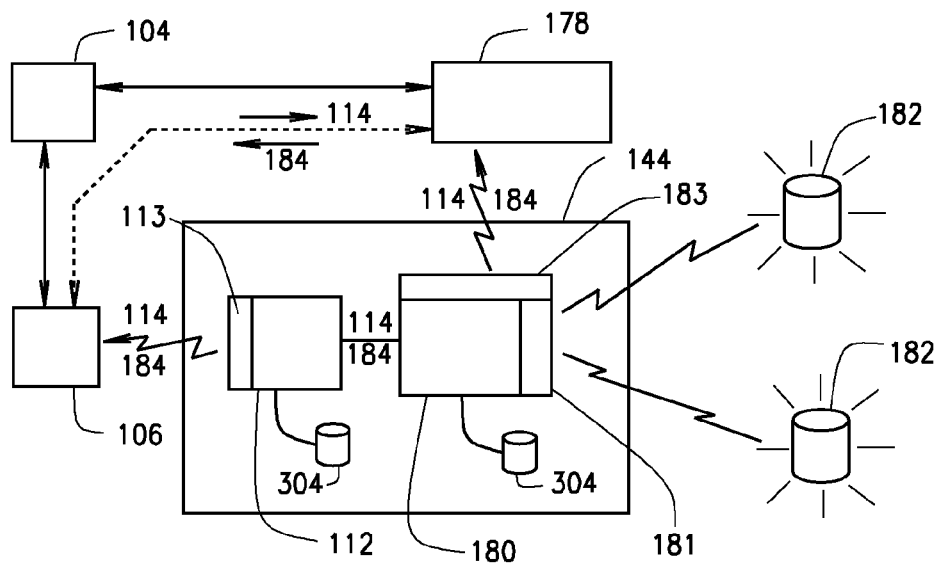
F I G. 4
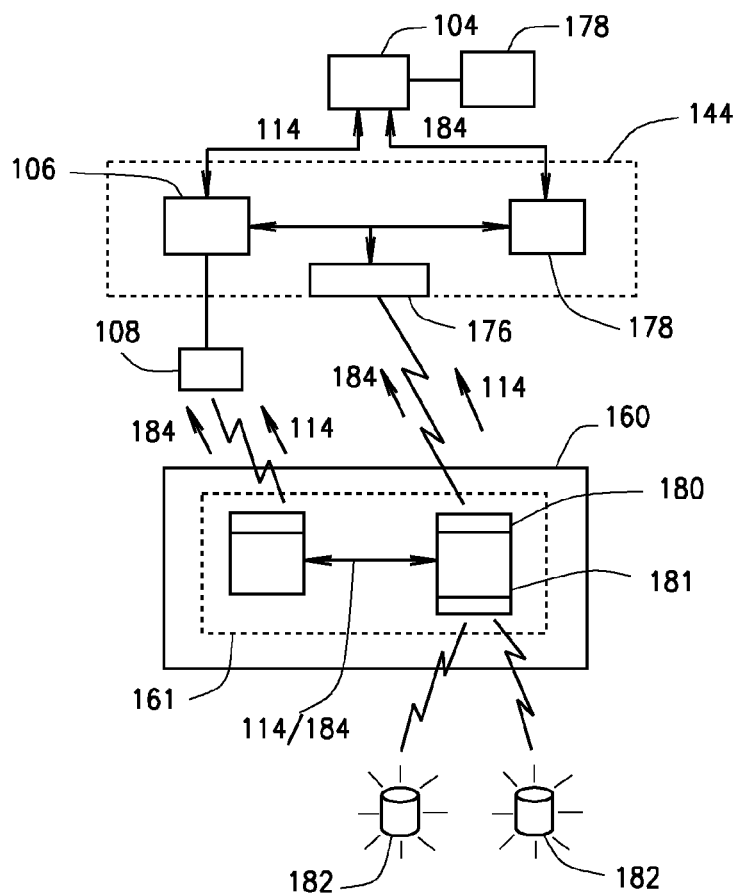
F I G. 5

(A) —READ | FROM | TAGSERIALNUMBER | TIME | PACKET# | EOM |
(B) —READ | FROM | PARTICIPANTNAME | TIME | PACKET# | EOM |
(C) —RESEND | FROM | DESTINATION | PACKET# | EOM |
(D) —TSYNC | FROM | IDENTIFIER | PACKET# | EOM |
(E) —LOOKUP | FROM | IDENTIFIER | PACKET# | EOM |
(F) —COMMAND | FROM | DEST | IDENTIFIER | PACKET# | EOM |
(G) —RSIG | FROM | TIME | EOM |
(H) —RQIMAGE | FROM | DEST | IDENTIFIER | COMPRESSION | PACKETSIZE | PSOCKET | EOM |
(I) —STIMAGE | FROM | DEST | IDENTIFIER | COMPRESSION | PACKETSIZE | PSOCKET | EOM |
(J) —GPSWAKE | FROM | DEST | LSOCKET | SETTINGS | BUFFER | EOM |
(K) —GPSRWAKE | FROM | DEST | LSOCKET | SETTINGS | BUFFER | EOM |
(L) —GPSRMESS | FROM | DEST | LSOCKET | SETTINGS | BUFFER | EOM |
(M) —GPSRSMESS | FROM | DEST | LSOCKET | SETTINGS | BUFFER | EOM |
(N) —GPSWAY | FROM | DEST | LSOCKET | SETTINGS | BUFFER | EOM |
(O) —GPSWAYP | FROM | DEST | LSOCKET | SETTINGS | BUFFER | EOM |
(P) —GPSSENDS | FROM | DEST | LSOCKET | SETTINGS | BUFFER | EOM |
(Q) —GPSSENDC | FROM | DEST | LSOCKET | SETTINGS | BUFFER | EOM |
(R) —GPSCLOSE | FROM | DEST | LSOCKET | EOM |

FIG. 6

SYSTEM AND METHOD OF AN EVENT TIMING SYSTEM HAVING INTEGRATED GEODETIC TIMING POINTS

CROSS-REFERENCE TO RELATED APPLICATIONS

This application is a National Stage of International Application No. PCT/US14/30537, filed on Mar. 17, 2014, which claims the benefit of U.S. Provisional Application No. 61/801,012, filed on Mar. 15, 2013. This application is also a continuation-in-part of U.S. application Ser. No. 13/980,545, filed on Jul. 18, 2013, that was a 371 National Stage of PCT/US12/022132, filed on Jan. 20, 2012, that claimed priority to U.S. Provisional 61/434,782, filed on Jan. 20, 2011; a continuation-in-part of U.S. application Ser. No. 13/582,148, filed on Aug. 31, 2012, that was a 371 National Stage of PCT/US11/026717, filed on Mar. 1, 2011, that claimed priority to U.S. Provisional 61/369,013, filed on Jul. 29, 2010, and also U.S. Provisional 61/309,259, filed on Mar. 1, 2010; and also a continuation-in-part of U.S. application Ser. No. 14/793,370, filed on Jul. 7, 2015, that was a continuation of U.S. patent application Ser. No. 13/194,880 (Now U.S. Pat. No. 9,076,278) that was filed on Jul. 29, 2011, that claimed priority to U.S. Provisional 61/369,013, that was filed on Jul. 29, 2010. This application is a continuation-in-part of U.S. application Ser. No. 14/374,757, filed on Jul. 25, 2014, which was a U.S. National Stage of PCT International Application No. PCT/US13/023167, filed on Jan. 25, 2013, which claimed the benefit of U.S. Provisional Application No. 61/590,782, filed on Jan. 25, 2012. This application is a continuation-in-part of U.S. application Ser. No. 13/980,539, filed on Jan. 18, 2013, which was a U.S. National Stage of PCT International Application No. PCT/US12/022,125, filed on Jan. 20, 2012, which claimed the benefit of U.S. Provisional Application No. 61/434,769, filed on Jan. 20, 2011. This application is a continuation-in-part of U.S. application Ser. No. 14/374,753, filed on Jul. 25, 2014, which was a U.S. national phase §371 application of PCT International Application No. PCT/US13/023274 filed on Jan. 25, 2012, which claimed the benefit of U.S. Provisional Application No. 61/590,667, filed on Jan. 25, 2012. The disclosure of each of these priority applications is incorporated herein by reference.

FIELD

The present disclosure relates to an event timing system and, more specifically, to an event timing system including a location tracking system for tracking the timed participant or object throughout the timed event.

BACKGROUND

The statements in this section merely provide background information related to the present disclosure and may not constitute prior art.

When using an RFID system or similar detection technology system for timing sporting events, it often desirable to track the progress of a participant. In current systems such as those used in marathons, an RFID tag reader is setup at the beginning or starting line, and one or more mid-points was waypoints such as at various distance location along the route of the marathon. Another final RFID tag reader is located at the finish line to provide the determination of the participant's time for traversing the marathon course.

Other systems, not used in current sport timing events, can track a location of an objection by using a GPS receiver that receives geodetic location data from a plurality of orbiting GPS or GIS satellites. These GPS receivers are often used in vehicles and can be handheld, but are not designed or suitable for use in most timed events such as running races. Furthermore, these GPS receivers often know their own location within a defined accuracy, and have been implemented in modern smart phone technology. These smart phones include a GPS receiver and can be program with software programming in an "app" for providing location data via the application to remote systems. However, the carrying and use of smart phones are not practical for use by event participants, especially where harsh conditions or water are present. Furthermore, these smart phones are not adaptable for use by a participant or an event organizer for integration with event timing systems and are themselves not accurate enough to be used for determining a participants event time.

As such, the inventor hereof has identified a need for a timing system having and RFID tag reader capability for identifying each event participant and for determining an accurate determination of the participants time in an event, but also that it would be desirable to obtain location data about each participant so that the progress of each participant can be monitored, tracked and displayed to remote systems such as remote displays.

SUMMARY

The inventor hereof has succeeded at designing systems and methods for capturing timed geographic location data of one or more moving object such as participants along a timed event route or course, associating such location data with each such object or participant, communicating the captured timed geographic location data to a timing system during such an event for monitoring, tracking, reporting and displaying of the location and movement of the object or event in near real time during an event and for having such location data for use after such an event.

According to one aspect, a system for determining a location along a route being traveled by a participant having a participant identifier that will be tracked and timed during an event with the system including a location device associated with the participant and the participant identifier. The location device has a location information receiver receiving location information from a location providing source and a location determination module determining a participant location from the received location information. It also has a wireless communication interface for transmitting the determined location as location data that includes the participant identifier. A location determination system is in at least periodic wireless communication with the wireless communication interface of the location device and receives the transmitted location data and determines a participant location from the received location data. A timing system receives the participant location from the location determination system and determines participant position along the route as a function of the received participant location. The timing system generates a participant location message over an output interface including at least one of the participant location and the determined participant route position.

According to another aspect, a system is provided for determining a route or waypoints along a route to be or being traveled by a participant having an RFID tag that will be tracked along such route such as during an event. The system includes a tag reader system that receives one or more tag reads from the RFID tag and determining a time for each tag read along with identifying the tag number of the RFID tag. The tag reader transmits a tag read message including at least a portion of the received tag reads with the tag number and the determines times and wherein the location device is associated with the RFID tag of the participant. A location device is associated with the participant and has a location data receiver for receiving location data from a location providing source. It also has a wireless communication interface. The location detection device receives location information from the location providing source, time stamps each received location information, and transmits location data associated with the location device over the wireless interface. The system also includes a location determination system in at least periodic wireless communication with the location device that receives the transmitted location data, and transmitting the received location data. An event/timing system receives the transmitted location data and receives the tag read message including the tag number from the tag reader. The timing system determines a route or a waypoint along a route to be or being traveled by a participant that will be tracked along such route such as during an event or tracking of the participant along the determined route. The timing system associates the location data with the RFID tag number as provided by the RFID tag reader from at least one of the tag reads from the tag associated with the location device.

According to still another aspect, a method of determining a location of a participant in a timed event having a participant identifier, the method includes a location device associated with the participant and the participant identifier performing the processes of receiving location information from a location providing source, determining a participant location from the received location information and transmitting the determined location as location data that includes the participant identifier. The method the processes at location determination system in at least periodic wireless communication with a wireless communication interface of the location device that includes receiving the transmitted location data and determining a participant location from the received location data. In a timing system, the method includes receiving the participant location from the location determination system, determining participant position along the route as a function of the received participant location, and generating a participant location message over an output interface including at least one of the participant location and the determined participant route position.

In another aspect, a method provides for determining a route or waypoints along a route to be or being traveled by a participant having an RFID tag that will be tracked along such route such as during an event. The method includes in a tag reader system the processes of receiving one or more tag reads from the RFID tag, determining a time for each tag read, identifying the tag number of the RFID tag, and transmitting a tag read message including at least a portion of the received tag reads with the tag number and the determined times. The method includes in a location device associated with the RFID tag of the participant and having a location data receiver, the processes of receiving location data from a location providing source, time stamping each received location information, and transmitting location data associated with the location device over the wireless interface. The method includes in a location determination system in at least periodic wireless communication with the location device the processes of receiving the transmitted location data, and transmitting the received location data. In an event/timing system, the processes of receiving the transmitted location data; storing the received location data; receiving the tag read message including the tag number from the tag reader; determining a route or waypoint along a route to be or being traveled by a participant that will be tracked along such route such as during an event or tracking of the participant along the determined route and associating the location data with the RFID tag number as provided by the RFID tag reader from at least one of the tag reads from the tag associated with the location device.

According to yet another aspect, a system and method for determining a route or waypoints along a route to be or being traveled by a participant, the system including a location device associated with the participant having a location data receiver for receiving location data from a location providing source, and a wireless communication interface, the location detection device receiving location information from the location providing source, time stamping each received location information, and transmitting location data associated with the location device over the wireless interface; a location detection device in at least periodic wireless communication with the location device for receiving the transmitted location data, and transmitting the received location data; and an event/timing system receiving the transmitted location data and storing the received location data, determining a route or waypoints along a route to be or being traveled by a participant that will be tracked.

Further aspects of the present disclosure will be in part apparent and in part pointed out below. It should be understood that various aspects of the disclosure may be implemented individually or in combination with one another. It should also be understood that the detailed description and drawings, while indicating certain exemplary embodiments, are intended for purposes of illustration only and should not be construed as limiting the scope of the disclosure.

BRIEF DESCRIPTION OF THE DRAWINGS

FIG. 4 is a block diagram of a participant's tag having an RFID timing chip and a location detection device and the wireless interfaces between the external components of a timing system according to one exemplary embodiment.

FIG. 5 is a block diagram of a participant's tag having a RFID timing chip with an integrated location detection device and a timing system having an integrated RFID tag reader and tag location detection system according to one exemplary embodiment.

FIG. 6 is a partial listing of communication messages and formats including the tag read data and location messages for supporting location determination as part of the time of passing determination that are suitable for use by the disclosed system and method.

It should be understood that throughout the drawings, corresponding reference numerals indicate like or corresponding parts and features.

DETAILED DESCRIPTION

Figure 1:
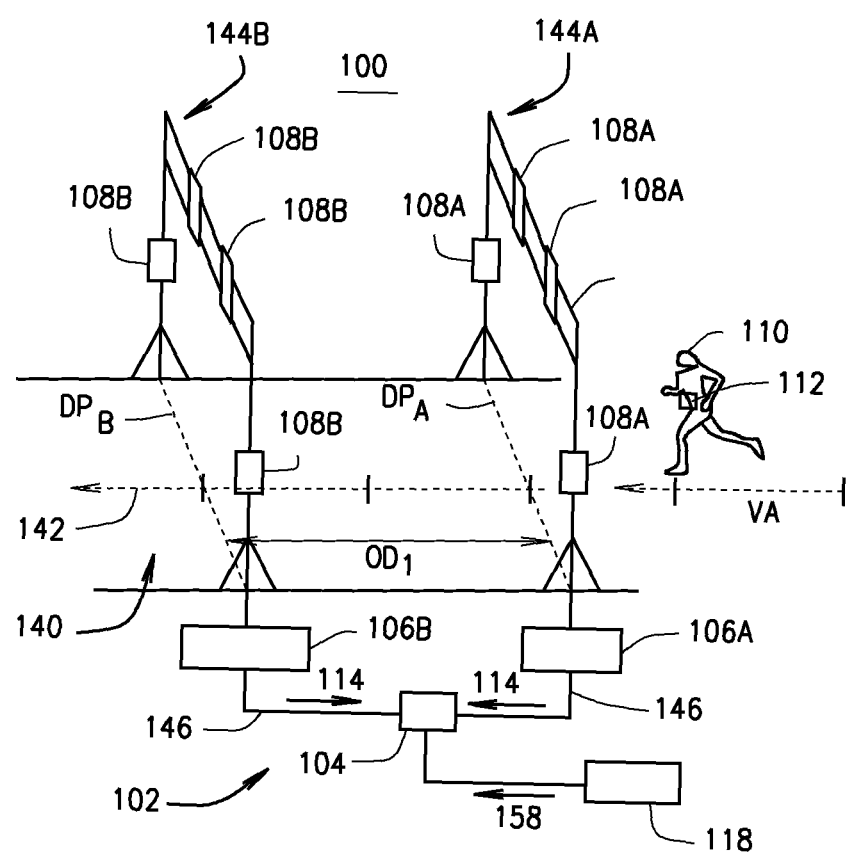
FIG. 1 is an illustration of a system and method for determining a time of a passing of a participant passed a detection line along a traveled route using RFID tags, antennas and RFID tag reader systems as known in the art.

The following description is merely exemplary in nature and is not intended to limit the present disclosure or the disclosure's applications or uses.

In one embodiment, a system for determining a location along a route being traveled by a participant having a participant identifier that will be tracked and timed during an event with the system including a location device associated with the participant and the participant identifier. The location device has a location information receiver receiving location information from a location providing source and a location determination module determining a participant location from the received location information. It also has a wireless communication interface for transmitting the determined location as location data that includes the participant identifier. A location determination system is in at least periodic wireless communication with the wireless communication interface of the location device and receives the transmitted location data and determines a participant location from the received location data. A timing system receives the participant location from the location determination system and determines participant position along the route as a function of the received participant location. The timing system generates a participant location message over an output interface including at least one of the participant location and the determined participant route position.

This can include at least one of the location device, the location determination system and the timing system, having a clock wherein such system/device can identify and/and associate a time of the location data and the timing system associates that location data time with the participant location and generates participant location message includes the location data time. The timing system can receive the location data as well the participant location.

In some embodiments, timing system receives location data associated with the route as route location data having a plurality of route location points. The timing system can then associate the participant location with at least one of the route location points and generate the participant location message to include the associated at least one route location point. This can includes a portion or all of the plurality of the route location points with the determined participant route position.

In some embodiments, the received location data of the route and the route location data can have a plurality of location points that is less than all of the locations along the route. In this embodiment, the timing system collects a portion of the received plurality of received participant locations and/or location data and generates a virtual location point of the participant within or proximate to the route. In some embodiments, the virtual location point is a virtual split point and the timing system determines a time of passing of the participant by the virtual point such as the virtual split point and also includes the determined time of passing the virtual point in its generated participant location message.

In some embodiments, the timing system does not include any route location data or route location points and the route of the participant is undefined. In such case, the timing system can collect a plurality of participant locations from a plurality of received participant locations and/or location data, and then maps or creates or otherwise generates a virtual route of the participant therefrom. As the participant travels about, the participant and the system described herein, creates a virtual route and can also determine times associated with the participants traversing of that route. Such a virtual route can be saved by the person for later travel and comparison. For instance, the timing system can determine the pace, the duration or a point of crossing a virtual waypoint of a participant along the route based on the received location data or the determined participant position along the route.

The location device can be configured to store the location data at intervals based on a predetermined rate or continuously or based on receiving a request or command. In one embodiment, the location device is configured to receive a location download request, and then transmits the location data over the wireless interface to the location determination system responsive to said received request. The location detection device can be configured to only transmit the received location data responsive to the location device receiving a request that a transmission to the location determination system is currently available.

A remote system can be communicatively coupled to the timing system to receive the generated participant location message. Such remote systems can include a display that displays the route and the participant location on a display map of the route or a map of the actual geodetic route traveled by the participant or the current participant location. These can include, but are not limited to, a Kiosk, a website, a mobile phone, a portable computer, a tablet, a news station, a social network, and a broadcast network.

In some embodiments, the location device is configured for selective activation and deactivation of its location information receiver and the wireless interface receives an activation and deactivation command from the location determination system. The location determination system transmits the activation and deactivation command responsive to a command message received from the timing system and the timing system is configured for generating the command message.

In some embodiments, the location determination system is transmits to the location device a location data request requesting all or a portion of the location data from the location device. The location device can then transmit the location data responsive to the location data request. This can include a dump all data and then clear all data command to the location device, in which the location device transmits all of its location data and then clears its memory.

In some embodiments, the system 100 or 102 can include an RFID tag having a radio frequency (RF) interface for transmitting an RFID tag read including the participant identifier associated with the RFID tag responsive to a tag read request. A compatible tag reader transmits the tag read request and in response receives a tag read from the RFID tag. The tag reader then determines a time for the received tag read and identifies the participant number associated with the tag read and transmits a tag read message over a timing system interface with the determined tag read time and the participant number. The timing system receives the tag read message including the tag number and tag read time from the tag reader and associates the received location data with the tag read and tag read time. The timing system then generates the participant location includes the tag read time In some embodiments, the location device is communicatively coupled with the RFID tag and provides the location data to the RFID tag. The RFID tag transmits the received location data to the location determination system or the tag reader. In some embodiments, the location device can also receive a location download request from the RFID tag, and transmit the location data over the wireless interface to the location determination system responsive to said received request from the RFID tag. The location detection device can in some embodiments be limited to only transmit the received location data responsive to the location device receiving an indicator request that the location device and RFID tag are within range of tag reader.

As addressed, herein, in some embodiment, at least one of the timing system and the tag reader system detects the proximity of the RFID tag to the RFID tag reader and transmits a location data download command to the location determination system. In response, that system in turn transmits a location data request to the location device and the location detection device transmits the location data responsive to the received location data request.

In other embodiments, the timing system transmits the location data associated with a particular RFID tag number responsive to a request from a remote system.

In various embodiments, a remote system is communicatively coupled to the timing system that generates a request to the timing system for the location data and in response receives the generated participant location message. Such remote systems, as described herein, can include a display that displays the participant location on a display map of the route or a map of the actual geodetic route traveled by the participant or the current participant location. Such as remote system can be a Kiosk, a website, a mobile phone, a PC, a tablet, a news station, a mobile app, a social network, and/or a broadcast network.

In another embodiment, a system is provided for determining a route or waypoints along a route to be or being traveled by a participant having an RFID tag that will be tracked along such route such as during an event. The system includes a tag reader system that receives one or more tag reads from the RFID tag and determining a time for each tag read along with identifying the tag number of the RFID tag. The tag reader transmits a tag read message including at least a portion of the received tag reads with the tag number and the determines times and wherein the location device is associated with the RFID tag of the participant. A location device is associated with the participant and has a location data receiver for receiving location data from a location providing source. It also has a wireless communication interface. The location detection device receives location information from the location providing source, time stamps each received location information, and transmits location data associated with the location device over the wireless interface. The system also includes a location determination system in at least periodic wireless communication with the location device that receives the transmitted location data, and transmitting the received location data. An event/timing system receives the transmitted location data and receives the tag read message including the tag number from the tag reader. The timing system determines a route or a waypoint along a route to be or being traveled by a participant that will be tracked along such route such as during an event or tracking of the participant along the determined route. The timing system associates the location data with the RFID tag number as provided by the RFID tag reader from at least one of the tag reads from the tag associated with the location device.

In another embodiment, a method of determining a location of a participant in a timed event having a participant identifier, the method includes processes in a location device associated with the participant and the participant identifier that include receiving location information from a location providing source, determining a participant location from the received location information and transmitting the determined location as location data that includes the participant identifier. The method includes processes preformed in a location determination system in at least periodic wireless communication with a wireless communication interface of the location device that include receiving the transmitted location data and determining a participant location from the received location data. In a timing system, the method includes receiving the participant location from the location determination system, determining participant position along the route as a function of the received participant location, and generating a participant location message over an output interface including at least one of the participant location and the determined participant route position.

This method can include in one or more embodiments the processes of at least one of the location device, the location determination system and the timing system having a clock and the method including identifying a time of the location data and the timing system associating the location data time with the participant location and the generating includes in the generated participant location message the location data time.

At the timing system the process can also include receiving location data associated with the route as route location data having a plurality of route location points and associating the received participant location with at least one of the route location points with the generating including in the generated participant location message the associated at least one route location point.

In some embodiments, where the system 102 includes RFID tag technology, the system includes an RFID tag having an RF interface that transmits an RFID tag read including the participant identifier associated with the RFID tag responsive to a tag read request. In a tag reader, the processes can includes transmitting the tag read request and receiving a tag read from the RFID tag in response to the transmitting, determining a time for the received tag read; identifying the participant number associated with the tag read, and transmitting a tag read message over a timing system interface with the determined tag read time and the participant number. In the timing system the process can include receiving the tag read message including the tag number and tag read time from the tag reader and associating the received location data with the tag read and tag read time; wherein the generating of the participant location includes the tag read time.

In another embodiment, a method provides for determining a route or waypoints along a route to be or being traveled by a participant having an RFID tag that will be tracked along such route such as during an event. The method includes in a tag reader system the processes of receiving one or more tag reads from the RFID tag, determining a time for each tag read, identifying the tag number of the RFID tag, and transmitting a tag read message including at least a portion of the received tag reads with the tag number and the determined times. The method includes in a location device associated with the RFID tag of the participant and having a location data receiver, the processes of receiving location data from a location providing source, time stamping each received location information, and transmitting location data associated with the location device over the wireless interface. The method includes in a location determination system in at least periodic wireless communication with the location device the processes of receiving the transmitted location data, and transmitting the received location data. In an event/timing system, the processes of receiving the transmitted location data; storing the received location data; receiving the tag read message including the tag number from the tag reader; determining a route or waypoint along a route to be or being traveled by a participant that will be tracked along such route such as during an event or tracking of the participant along the determined route and associating the location data with the RFID tag number as provided by the RFID tag reader from at least one of the tag reads from the tag associated with the location device.

In some embodiments, a system and method for determining a route or waypoints along a route to be or being traveled by a participant, the system including a location device associated with the participant having a location data receiver for receiving location data from a location providing source, and a wireless communication interface, the location detection device receiving location information from the location providing source, time stamping each received location information, and transmitting location data associated with the location device over the wireless interface; a location detection device in at least periodic wireless communication with the location device for receiving the transmitted location data, and transmitting the received location data; and an event/timing system receiving the transmitted location data and storing the received location data, determining a route or waypoints along a route to be or being traveled by a participant that will be tracked.

One or more embodiment can include various features selected alone or in combination from the following list: a) The timing system receives the location data for a route and the timing system establishes the GPS-based route from such received data; b) The timing system establishes one or more GPS-based waypoints along such GP-based route; c) The timing system receives a plurality of location data and determines an estimate of a time of passing of the participant past one of the GPS-based waypoints or along the GPS-based route; d) The timing system determines at least one of a pace, a duration or a point of crossing a waypoint of a participant along the route based on the received location data; e) The location device stores location data at intervals based on a predetermined rate. This can be determined by the timing system or otherwise such as predetermined and stored or based on the particular event, and the location device receives programming instructions for establishing the predetermined rate; f) The location device receives a GPS download request, and wherein the location device transmits the determined location over the wireless interface to a location detection device responsive to said request. g) The location detection device only transmits the received location data responsive to the location detection device receiving an input that a transmission to the location detection device is currently available; h) A remote system requests location data from the timing system, receive the requested location data, and to display the location data on a display map of the route and/or the actual traveled route traveled by the participant or the most recent and current location of the participant. The remote system can be a Kiosk, a website, a mobile phone, a PC, a tablet, a news station, or a broadcast network; i) The location device selectively activates and deactivates its location data receiver, and wherein the wireless interface receives activation and deactivation commands, and the location detection system transmits the activation and deactivation commands responsive to a message received from the timing system; j) The location detection system transmits to the location tag a location data request requesting all or a portion of the location data from the location device, and the location device transmits the location data responsive to the location data request; k) The location detection system transmits a dump all data and then clear all data commands, and the location device transmits all of the location data and then clear a memory associated with the location device; l) The location providing source is a plurality of GPS satellites and wherein the location data is GPS data; m) The participant has an RFID tag during an event, the system further includes a tag reader system receiving one or more tag reads from the RFID tag, determining a time for each tag read, identifying the tag number of the RFID tag, and transmitting a tag read message including at least a portion of the received tag reads with the tag number and the determined times and wherein the location device is associated with the RFID tag of the participant. The timing system receives and stores the tag read message including the tag number from the tag reader and associates the location data with the RFID tag number as provided by the RFID tag reader from at least one of the tag reads from the tag associated with the location device; n) The location device includes the RFID tag number of the associated RFID tag for the participant; o) The location device is communicatively coupled to the RFID tag; p) The location device receives a GPS download request, and wherein the location device transmits the tag location over the wireless interface to a location detection device responsive to said request; q) At least one of the timing system and the tag reader system detects the proximity of the RFID tag to the RFID tag reader and transmits a location data download command to the location detection system, and wherein the location detection device transmits the GPS download request to the location device; r) The timing system transmits the location data associated with a particular RFID tag number responsive to a request from a remote system; and/or s) A remote system configured to request location data from the timing system, receive the requested location data, and to display the location data on a display map of the route indicating the route traveled by the participant or the most recent and current location of the participant.

In another embodiment, a system provides for determining a route or waypoints along a route to be or being traveled by a participant having an RFID tag that will be tracked along such route such as during an event. The system includes a tag reader system receiving one or more tag reads from the RFID tag, determining a time for each tag read, identifying the tag number of the RFID tag, and transmitting a tag read message including at least a portion of the received tag reads with the tag number and the determined times and wherein the location device is associated with the RFID tag of the participant. The system also includes a location device associated with the participant having a location data receiver for receiving location data from a location providing source, and a wireless communication interface, the location detection device receiving location information from the location providing source, time stamping each received location information, and transmitting location data associated with the location device over the wireless interface. The system further includes a location detection device in at least periodic wireless communication with the location device for receiving the transmitted location data, and transmitting the received location data. An event/timing system receiving the transmitted location data and storing the received location data and receiving and storing the tag read message including the tag number from the tag reader, the timing system determining a route or waypoints along a route to be or being traveled by a participant that will be tracked along such route such as during an event or tracking of the participant along the determined route and associating the location data with the RFID tag number as provided by the RFID tag reader from at least one of the tag reads from the tag associated with the location device.

As described herein one or more of the features of the present system include 1) capturing location such as GPS coordinates along the course of an event and mapping the coordinates to create virtual split points for that event; 2) taking timing data from one or more points along the course and estimating the time when a participant crossed through a virtual split point; 3) taking location/GPS data from a cell phone or dedicated GPS device, as well as timing data from one or more RFID read points along the course and estimating the time when a participant crossed through a virtual split point; 4) taking timing data for a participant from any race or event, and overlaying that data onto a different event, thereby simulating performance in that event, by providing simulated or virtual timing/detection points; 5) determining a pace of a participant at a virtual timing point by using various RFID timing points with location/GPS coordinates and comparing the time of a chip read between the two RFID timing stations; and/or 6) creating a virtual race courses on the fly without specific course directions by utilizing GPS coordinates and relaying those coordinates to other participants during an event. The use of RFID stations along the course allows the system to monitor progress of participants, and the integration of RFID tag reads along with the GPS coordinates makes it possible to re-create the race at a later time, thus facilitating the analysis of the event.

Referring now to the Figures, FIG. 1 is a system 100 that includes an event participant management system 102 illustrating event participation system 102 with a timing system 104. The timing system 104 includes one or more tag readers 106 and antenna 108. A participant 110 travels along event course 140 and participant travel path 142 therein and traveling at a speed of VA. The participant has an RFID tag 112 (sometimes referred as a chip) that has a unique tag identifier. As shown in FIG. 1, the system 100 can include more than one timing point shown as two timing/detection points DPA and DPB that are spaced apart by distance OD1. Timing point DPA is monitored by participant identification system 144A using tag reader 106A using antenna 108A and timing point B is monitored by participant identification system 144B using tag reader 106B using antenna 108B. Each tag readers 106A and 106B (referred commonly as tag reader 106) using the antenna 108A and 108B, respectively (referred commonly as antenna 108) obtains a plurality of an RFID tag read messages 114 (referred herein shortened as tag read 114) that includes the tag identifier, and transmits the tag identifier to the timing system 104 as the participant 110 traverses along path 142.

As shown the timing system 104 is coupled to both tag reader reading systems, a first participant identification system 144A is located along course 140 at point A and includes a plurality of antenna 108A coupled to tag reader 106A. A second participant identification system 144B is located along course 140 at point B that includes antenna 108B coupled to tag reader 106B. Point A is spaced apart from point B at a distance OD1 along course 140. Distance OD1 can be only few feet or can be split points such as miles or kilometers apart along course 140, such as a start line, a split point or a finish line, by ways of example. Each tag read 114 and associated measured biometric data 120 is correlated to the particular point A and point B and such can be provided to biometric module 116 for use in analysis and reporting.

As shown, as the participant 110 with RFID tag 112 approaches and passes each of points A and B, each participant identification system 144A, 144B receives one or more tag reads 114 from the RFID tag 112 using tag readers 106A, 106B transmits each tag read 114 to the timing system 104 via communication link 146. A participant registration system 118 is communicatively coupled to timing system 104 for providing participant information such as registration information, assignment of a unique tag identifier to each registered participant 110 and therefore assignment of each RFID tag 112 to each participant 110. Furthermore, the participant registration system 118 can provide other features and participant data 158 such as requests for desired outputs and notifications as to the progress or status of the participant 110 that can include the identification of determined geodetic timing points as will be described or one or more virtual detection points VDP that may define for the particular user the route 140 and/or the participant path 142 traveled by the participant 110 along the route 140 as will be further described herein.

Figure 2:
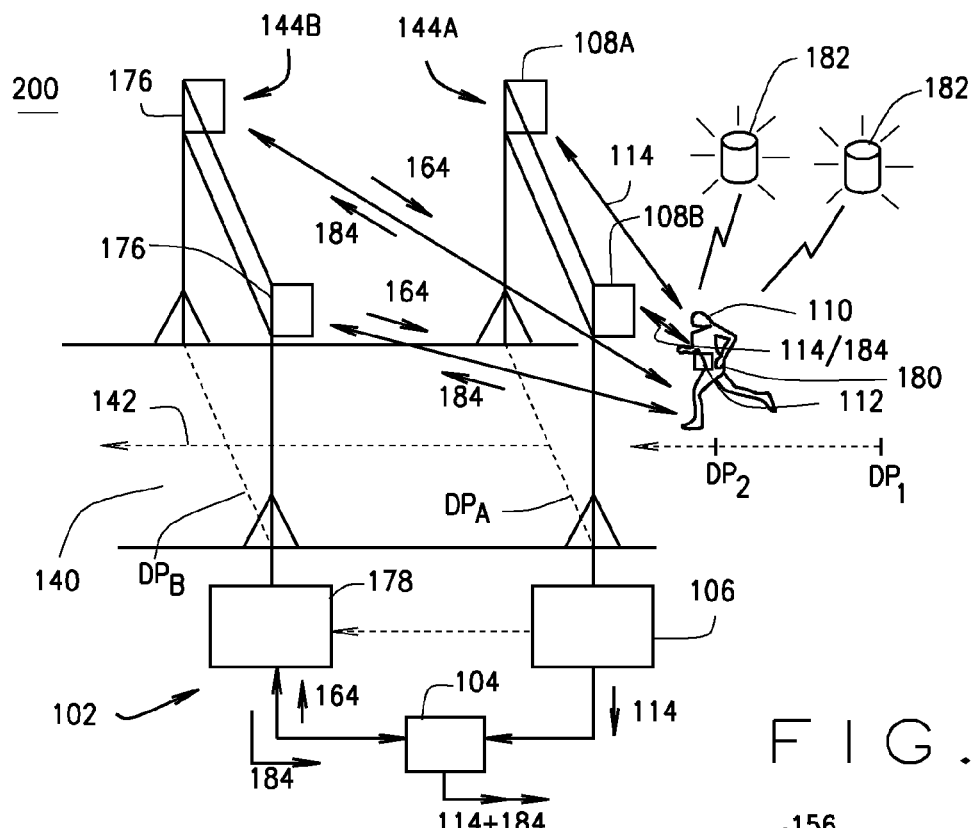
FIG. 2 is a schematic drawing showing a detection point along a racecourse having an RFID tag reader supplemented with a location detection system (LDS), according to one exemplary embodiment.

FIG. 2 is a schematic drawing showing a detection point along a racecourse having a first participant detection point 144A at position DPA and a second participant detection point 144B at position DPB that is spaced apart from the first detection point 144A along route 140 at a distance OD. In this embodiment, a RFID tag reader 106 is positioned at detection point 144A with RFID antenna 108A and 108B obtaining RFID tag reads 114 from the RFID tag 112 of the participant 110 when the tag 112 comes within communicative proximity with the antenna 108. In this example, the RFID tag reader 106 can obtain tag reads 114 when the participant 110 is at detection point DP1 and then again at DP2.

The detection point 144 in contrast in this example, supplements detection point 144A not with additional RFID tag readers 106, but rather utilizes a location detection system 178 having one or more location detection receivers 176 (also in some embodiments transceivers) associated therewith. The participant 110 not only has an RFID tag 112 but also has a location device 180. The location device 180 is configured to obtain and/or determine its geodetic location such as at DP2 based on received location messages received from location transmitters 182 that can be GPS satellites, cellular towers, or other wireless transmitters that may be positioned along the course 140 for providing a location indicator to location device 180. The location device 180 can then transmit location data 184 that includes the current and possibly past location data to location system transceivers 176 for providing to the location detection system 178.

As shown, in some embodiments, the location detection system 178 or the timing system 104 can send a location data request 164 from the location transceivers 176 to request the location device 180 transmit the location data 184. The location detection system 178 and the transceivers 176 can utilize wireless technology such as Wi-Fi or can utilize the mobile telephone network or a satellite network in other embodiments. The location detection system 178 can provide the received location data 184 to the timing system. The location device 180 can also be configured to transmit a participant name or number such as the tag number associated with the RFID tag 112 so that the location data 184 includes the participant identification along with the geodetic data. Further, in some embodiments, the location device 180, the location detection transceiver 176, the location detection system 178 and/or the timing system can associate a time or add a current time stamp or message with the location data 184 similar to the tag reader 106 adding a tag read time in the tag read 114.

Figure 3:
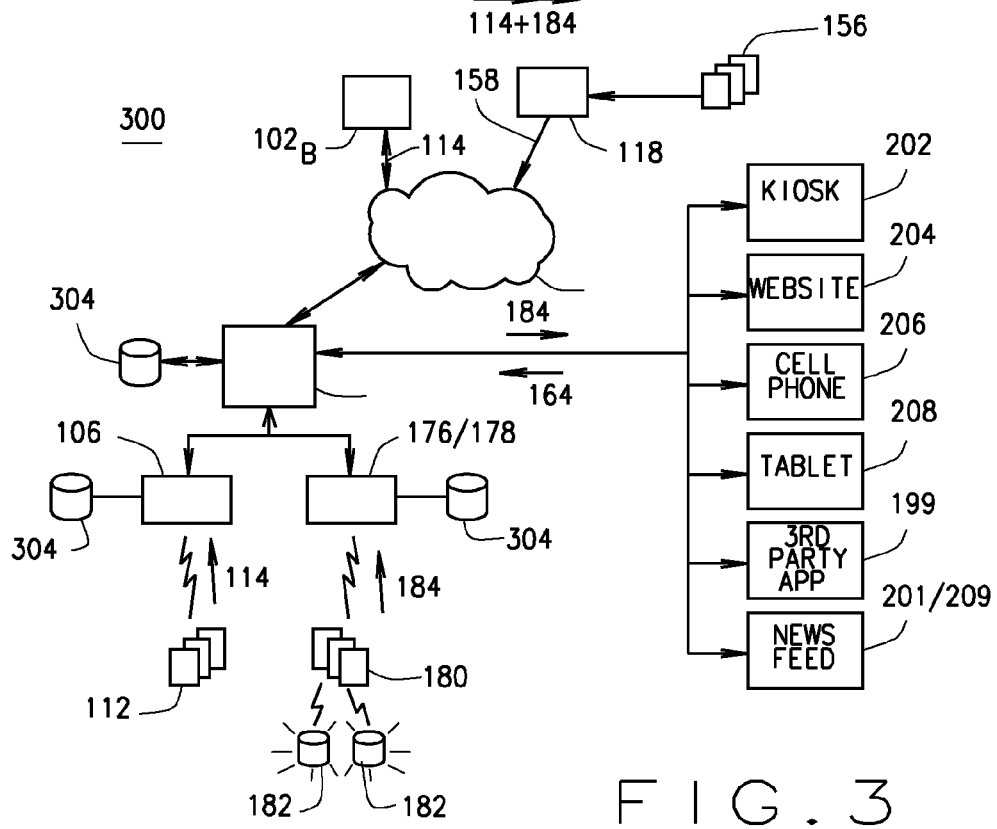
FIG. 3 is a schematic block diagram of an architecture and communication system for a timing system coupled via a timing system communication network for obtaining, storing and processing of participant location data as obtained during an event and the providing of such location data to coupled systems, according to one exemplary embodiment.

FIG. 3 is schematic block diagram of an architecture and communication system for an event management system 100 that has a timing system 104 coupled via a timing system communication network 320 for obtaining, storing and processing of participant location data 184 as obtained during the event and the providing of the received location data 184, or a determined geodetic location 184 based thereon to one or more coupled systems. As shown, timing system 104A is similar to that shown and described with regard to FIG. 2. Each of the tag reader 106, the location detection system 178, the location transceiver 176 and the timing system 104A includes a processor (not shown) and a memory 304 such as separate or common memory as described below. A second similar timing system 104B is also communicatively coupled to the timing system 104A via the network 320.

A participant registration system 118 is coupled to one or more participant user devices 156 for receiving user input data 158 associated with an event including data specific to the user such as name, participant number, requests for outputs and reports and images, and location data 184 by ways of example. The timing system 104A receives inputs from each of these systems. When the timing system 104A receives that location data 184 of the participant 110 during the event, the timing system 104A can provide location data 184 along with timing data and tag read data over an output interface to communicatively coupled systems. The output or reporting systems can include, but is not limited to, a kiosk 202, a website 204, a mobile phone 206 such as via a voice call, a text message, an alert, an image, or an updating of a mobile application, a tablet compute, a third party system or application or a new feed. In any of these embodiments, the provided geodetic data 184 is provided in a format to enable the receiving device to display an image that includes or is based on the location data 184 and the identification of such location data with the participant 110. For instance, as will be described this can include updating an image of a map.

As addressed above, the location device 180 is usually associated with or place on the body or an article of clothing of the participant 110 during an event that can be in addition to an RFID tag 112 that is often carried by the participant 110. The location device 180 can be separate and apart from the RFID tag 112, such as when the participant 110 carries a mobile phone with a location device 180 built therein and the mobile phone is configured with location enabled mobile application. However, in some embodiments, the location device 180 can be associated with and/or integrated with the RFID tag 112 that can provide additional functionality and features. As shown in FIGS. 4 and 5, there are various embodiments where the participant tag 144 includes the RFID tag 112 with an RFID interface 113 over which the tag read 114 is transmitted to the tag reader 106. The participant tag 144 also includes the location device 180 that is communicatively coupled to the RFID tag 112 over which the tag read 114 with the participant/tag number can be provided to the location device 180 and/or the location data 184 can be provided by the location device 180 to the RFID tag 112.

In one or both of such embodiments, the RFID tag 112 can transmit not only the tag read 114 but also the location data 184 to the tag reader 106 for transmitting therefrom to the timing system 104 or to the location detection system 178. In the other embodiment, the location device 180 can transmit the tag number within the received tag read 114 from the RFID tag 112 with the location data 184 or can also transmit the entire tag read 114 therewith. The location device 180 includes a location receiving interface 181 for receiving location signals from location transmitters as well as a wireless interface 183 for wirelessly transmitting the location data 184 to the location detection system 178. This again can be any suitable wireless communication interface, network and technology. FIG. 5 different slightly from FIG. 4 in that the participant detection system 144 of FIG. 5 reflects that the location transceiver 176 can be shared with the tag reader 106 or communicatively coupled thereto. Further, the participant tag 160 of FIG. 5 reflects the manufacture of both RFID tag 112 and the location device 180 on a common mounting surface 161 such as a common piece of Mylar.

FIG. 6 is a partial listing of communication messages and formats including the tag read data and location messages for supporting location determination as part of the time of passing determination that are suitable for use by the disclosed system and method. For the location detection system, the following messages have been developed for communication between the various system 100 and system 102 components as described herein, including, but not limited to, the timing system 104, the location detection system 178, the location detection transceiver 176, the tag reader 106, the RFID tag 112, and the location device 180.

GPS Wakeup Message (GPSWAKE): The GPSWAKE message is sent to by a timing system 104 to the location detection system 178 or location detection transceiver 176 or tag reader 106 or location device 180 to request that a communication session begin related to a GPS read or determination. Receipt of this message by a GPS enabled location device 180 or location device transceiver 176 to send back parameters for the session in the buffer that sensed and received the GPS data from the location device 180. The LSOCKET value can be used to identify a unique socket being used for the session. The SETTINGS value is used to request the timing system 104 or TRS conform to specific parameters for the session. Once a session is established, the requesting entity will wait for data to show up in the buffer and process it accordingly. Thus, this message is sent to a GPS enabled TRS when setting up a long-term session where GPS read data will trickle in over time, into the Buffer allocated.

---

Packet length = variable size
Total fields = 7
GPSWAKE|FROM|DEST|LSOCKET|SETTINGS|BUFFER|EOM|

---

GPS Wakeup and Receive Message (GPSRWAKE): The GPSRWAKE message is sent to location detection system 178 or tag reader 106 or to the location device 180 to request that a communication session begin with GPS data being returned immediately. This message causes the GPS enabled chip or GPS enabled tag reader 106 to send back GPS location and possibly also the time information in the GPS reader or tag reader 106 having received the message and having had at least one location device 180 being detected by such system. The LSOCKET value can be used to identify a unique socket being used for the session. The SETTINGS value is used to request the timing system 104 or tag reader 106 conform to specific parameters for the session. Once the initial data has been received by the requesting entity, the session will remain open and wait for additional data to appear in the buffer of the requested entity. This command differs from the GPSWAKE message since the GPSWAKE does not request data, but only activates the GPS enabled tag reader 106 to wait for the next available GPS read data, when it occurs, e.g., the GPSWAKE message waits for data to show up. In contrast, the GPSRWAKE message requests that all GPS data 184 be sent immediately by the receiving entity, thus clearing the buffer of the receiving entity such as a GPS enabled tag reader 106 and location device 180.

---

Packet length = variable size
Total fields = 7
GPSRWAKE|FROM|DEST|LSOCKET|SETTINGS|BUFFER|EOM|

---

GPS Receive Message (GPSRMESS): The GPSRMESS message is sent to timing system 104 or tag reader 106 or location device 180 for location device 180 data reading to request that all data be transmitted immediately by the receiving system. This is a stateless message that does not require a session to first be created between the requesting and receiving entities. Therefore, the GPSRMESS message can be used in situations where rapid communications with a GPS or SGOS tag reader 106 requires, such as a verification of a prior read or in a situation the requesting timing system 104 determines from other facts or factors. The LSOCKET value can be used to identify a unique socket being used to receive the data. The SETTINGS value is used to request a communicatively coupled component or system to conform to specific parameters for the data transmission. BUFFER will contain the actual data coming back to the caller.

---

Packet length = variable size
Total fields = 7
GPSRMESS|FROM|DEST|LSOCKET|SETTINGS|BUFFER|EOM|

---

GPS Re-Send Message (GPSRSMESS): The GPSRSMESS message is sent to a timing system 104 or tag reader 106 or location device 180 to request that the data previously sent, be re-transmitted. This message can be used to retrieve data that may have been lost in route from the requested entity (another timing system 104 or tag reader 106 or location device 180) to the requesting entity such as another timing system 104. This is a stateless message that does not require a session to first be created. Thus, it is ideal for rapid communications with a chip or system. The LSOCKET value can be used to identify a unique socket being used to receive the data. The SETTINGS value is used to request a communicatively coupled component or system to conform to specific parameters for the data transmission. BUFFER will contain the actual data coming back to the caller.

---

Packet length = variable size
Total fields = 7
GPSRSMESS|FROM|DEST|LSOCKET|SETTINGS|BUFFER|EOM|

---

GPS Waypoint Message (GPSWAYP): The GPSWAYP message is sent to a chip or remote system to request specific data that is based on a specific or range of waypoint values. This is a stateless message that does not require a session to first be created. Thus, it is ideal for rapid communications with a chip or system. The LSOCKET value can be used to identify a unique socket being used to receive the data. The SETTINGS value is used to request a communicatively coupled component or system conform to specific parameters for the data transmission. BUFFER will contain the actual data coming back to the caller.

---

Packet length = variable size
Total fields = 7
GPSWAYP|FROM|DEST|LSOCKET|SETTINGS|BUFFER|EOM|

---

GPS Send Message (GPSSENDS): The GPSSENDS message is sent to another timing system 104 or tag reader 106 or location device 180 to transmit GPS data 184 be sent immediately. This message requires you to first create a session. The TSOCKET value can be used to identify a unique socket on the remote system. The SETTINGS value is used to request a communicatively coupled component or system to conform to specific parameters for the data reception. BUFFER will contain the actual data being sent. The advantage to using the GPSSENDS message is that the remote system will automatically handle error handling for lost messages that did not arrive.

---

Packet length = variable size
Total fields = 7
GPSSENDS|FROM|DEST|LSOCKET|SETTINGS|BUFFER|EOM|

---

GPS Send Message (GPSSENDC): The GPSSENDC message is sent to a timing system 104 or tag reader 106 or location device 180 to transmit data immediately. This message does not require a session. The TSOCKET value can be used to identify a unique socket on the remote system. The SETTINGS value is used to request another communicatively coupled component or system to conform to specific parameters for the data reception. BUFFER will contain the actual data being sent.

```
Packet length = variable size
Total fields = 7
GPSSENDC|FROM|DEST|LSOCKET|SETTINGS|BUFFER|EOM|
```

GPS Close Message (GPSCLOSE): The GPSCLOSE message is sent to another timing system 104, or tag reader 106 or location device 180 to inform it that transmissions regarding location data 184 are now over and the sockets being used for location data 184 have been released. The TSOCKET value can be used to identify a unique socket on the remote system. This message is used for sessions that are always open as described above, for example, GPSWAKE, GPSRWAKE.

```
Packet length = variable size
Total fields = 5
GPSCLOSE|FROM|DEST|LSOCKET|EOM|
```

The GPSSENDC is used to send data to another system, which could be any device including a laptop computer, network file server, or another RFID reader. We also have the GPSSENDS message as well. The only difference is that the GPSSENDS message is used for session-oriented communications where the remote system is able to process packets and look for errors that can cause it to send a message back letting the sender know that the data didn't arrive correctly. The GPSSENDC doesn't require a session and it looks like a UDP datagram and is a connectionless packet. This makes it faster and easier to work with, but it doesn't have any built in error correction.

The buffer field contains information related to the GPS data. In fact, the buffer could also contain RFID information as well. For example, a basic message buffer might have something like the following GPS number, Total Satellites, Uptime, Longitude, Latitude, Offset, Current Time, and Elevation. The buffer is free-form text meaning the user can implement their own formatting within the buffer to determine delimiters between the data elements. As an example, a timing system 104 might use the # character to designate the end of each field within the buffer. Thus, I might have a packet that has a buffer containing something like: 34.56575#121.456487#18:00:03#0.564#234.

Any known GPS receiver ID can also be transmitted with the GIS location data 184.

In one embodiment, the GPS data is sent without waiting for the remote system to setup a connection socket. This is because in future implementations, we will be using multiple VPN ports to send messages back to the timing system 104 or perhaps any other system. Presently, the timing system 104 listens for any and all messages on a common socket, but this can also be provided to enable the user to designate a socket in real-time. The GPSSENDC message will be used for that purpose and when the receiving system collects a packet with the GPSSENDC header, it will parse the buffer to look for specific information regarding the desired communication parameters coming from the sender.

One example, of the waypoint message GPSWAYP, is where there may be a detection point along the course needs to collect data from the chips on the runners and the race has 50,000 participants in it. Now assume this detection point is at mile 5. There will be thousands of runners coming through that detection point very rapidly, thus the density will be very high. If the timing system 104 tried to collect every GPS data point from them, it would take a while (relative term) to collect the data for every 2 feet of resolution. During the first part of the race, it is less likely to need or track the runner's position every 2 to 3 feet. Most situations you can have data for every 50 to 100 feet. Thus, this message GPSWAYP allows the timing system 104 to tell the chip on the runner that we don't need all of the data, just a portion of it. The communications are much faster that way and we can handle very large densities of runners. The Settings is a free-form field that can be customized by the user. However, it is also possible to send a message such as: GPSWAYP|FROM|DEST|LSOCKET|Res:10|BUFFER|EOM| The value of Res:10 could mean to send us the data point for every 10 seconds from the GPS information collected. Thus, let's say the runner was on the course so far for 20 minutes and this is the first time we are collected the positional data, we will be asking for 6 samples per minute× 20 minutes=120 pieces of data. A GPS receiver can provide data down to 100th of a second and thus if we simply requested all data, we might have thousands of data points and that would take a long time to send from the runner's chip to the timing system. So, the GPSWAYP message allows the timing system 104 to decide how much data it will need and this can be change changed in real-time based on the density of runners the timing system 104 is seeing from the GPS reads.

The process of sending an acknowledgement could also be added. This could be something like GPSACK: GPSACK|FROM|DEST|LSOCKET|BUFFER|EOM.

In other embodiments, the process of sending an ACK requires more round trip time, which is not good when dealing with high densities of packets. This is much like the old UDP vs. TCP/IP argument. TCP/IP has the advantage of being a session protocol that has error correction through ACKs. UDP is much faster for sending bulk data because it requires no ACK. For the timing system 104, it may be desirable to dump the location data 184 rapidly to a tag reader 106, a location detection system 178 or location detection device 176 or timing system 104 without having the overhead of the ACKs. So, I think it would make sense to go ahead and add the ACK message in our spec. Thus, here is the format we will use:

The buffer will contain a response code which will likely be a value of 0 for failure and 1 for success. The timing system 104 could also use other values such as 2 or 3 for error handling.

Figure 7:
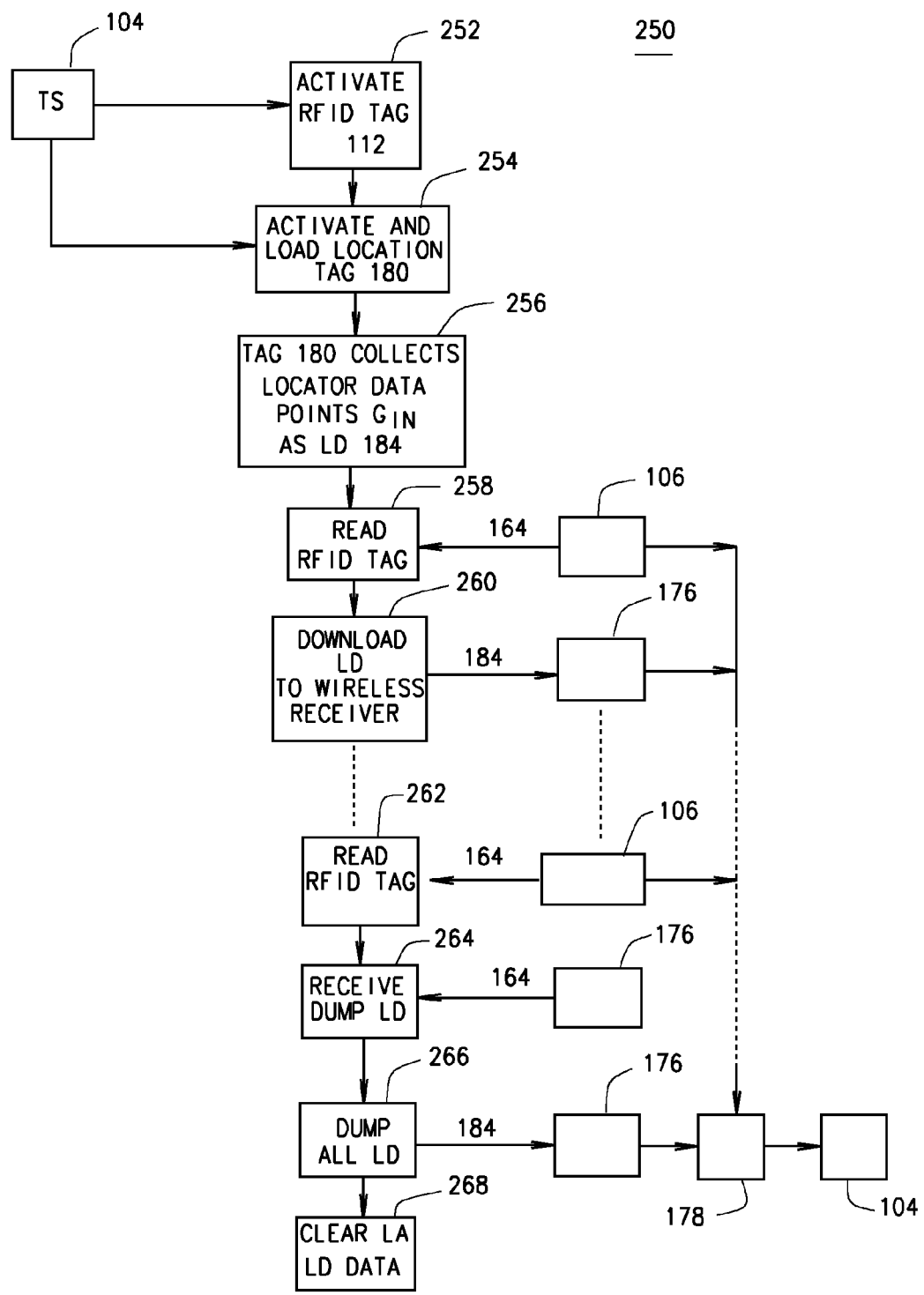
FIG. 7 is a flow chart of a process for integrating a location tag with an RFID tag for a participant in an event and the reading of the RFID tag and the location tag during the event as the participant traverses the event course at numerous location detection points along a course according to one exemplary embodiment.

FIG. 7 is a flow chart of a process for integrating a location device 180 with an RFID tag 112 for a participant 110 in an event and the reading of the RFID tag 112 to obtain a tag read 114 and the location device 180 to obtain the location data 184 during the event as the participant 1110 traverses the event course at numerous location detection points 144 along a course according to one exemplary embodiment. The timing system 104 implements the activation of the RFID tag 112 in process 252. The timing system 104 also activates and loads necessary participant and system information and data into the location device 180 in process 254. Processes 252 and 254 are typically performed prior to the participant 110 participating in the event. Once the participant 110 moves about route 142, whether as a part of the event course 140 or separate from any pre-defined course 142, the location device 180 collects location data 184 in process 256 that can be many different geodetic locations presuming the participant is not stationary.

When the participant comes within range or in proximity to a tag reader 106, the tag reader 106 or the location transceiver 176 can transmit a location request 164 to the RFID tag 112 and/or the location device 180. In process 258, the location device 180 receives the request 164 either directly or from the communicatively coupled RFID tag 112 and creates, transmits or otherwise downloads the location data 184 to the location transceiver 176. As the location device 180 has most likely been moving for a period of time, the location data 184 can include many different geodetic locations and each of these can be time stamped indicating the time when the locations device 180 received or determined each geodetic location within the location data 184. This is referred as a download in process 260 but can be a transmission of the data depending on the amount of data stored on the location device 180 and the size of its memory 304. This is repeated numerous times as indicated by process 262 as the participant 110 continues to move and come in contact or proximity with additional tag readers 106 or location transceivers 176. This can conclude in process 264 when a request is received by the location device to dump all location data 184 and which in process 266 the location device downloads or dumps all remaining location data 184 to the location transceiver 176. After this, the location device 180 can clear its memory 304 of all location data 184. The received location data 184 being obtained through this process can be provided to the location detection system 178 and/or to the timing system 104.

Figure 8:
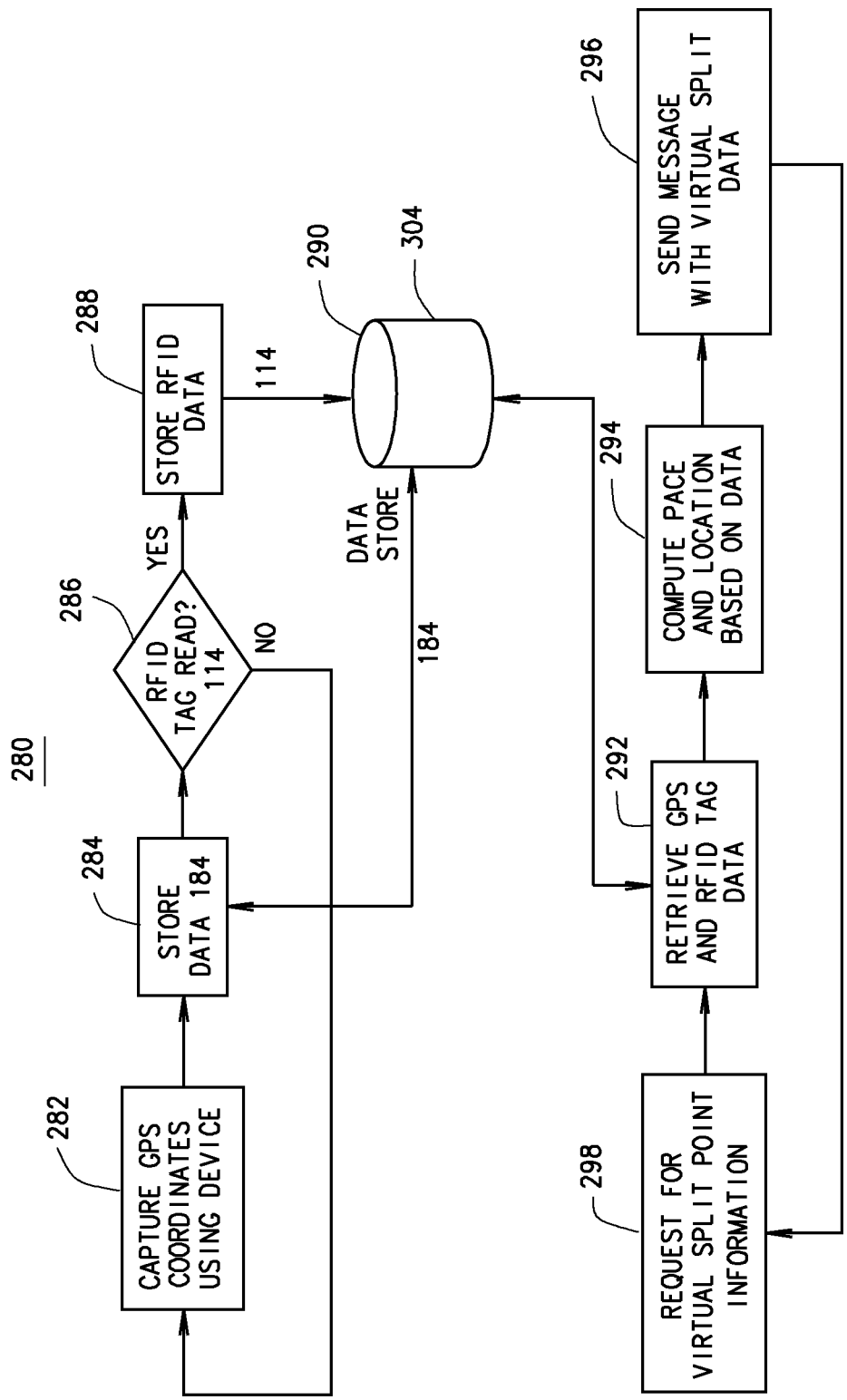
FIG. 8 is a flow chart of a process for processing GPS and RFID tag data by a timing system and establishing virtual split points along a route according to one embodiment.
Figure 9:
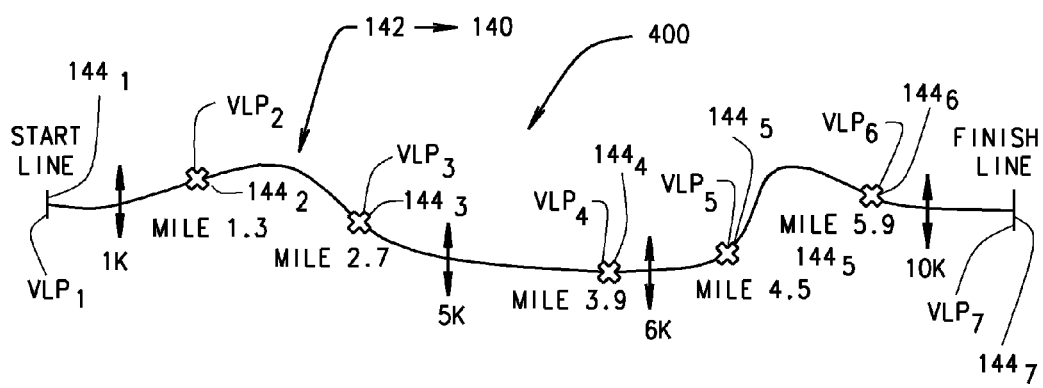
FIG. 9 illustrates the use of a mobile device such as a mobile phone equipped with a location tracking device to geographically define locations for a route and to also map or identify virtual location or split points along the course according to one exemplary implementation.
Figure 10:
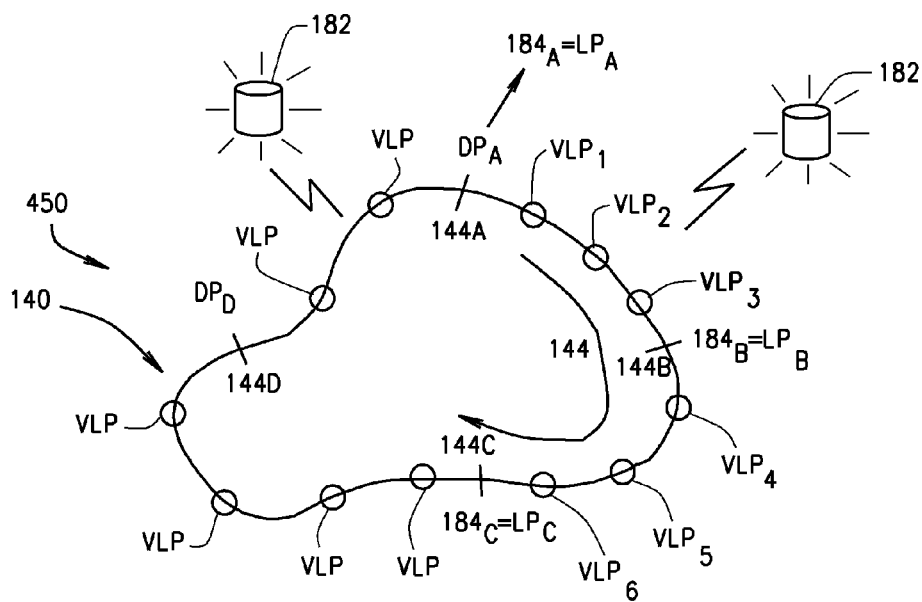
FIG. 10 is an illustration of an event course wherein multiple location detection points provide for the near real time providing of location data to an integrated RFID tag reading timing system according to one exemplary embodiment.

FIG. 8 is a flow chart 280 of a process for processing location data 184 and RFID tag reads 1114 by a timing system 104 and using such for establishing virtual location points VLP such as a could be a virtual detection point 144, a timing point such as a split point or a virtual route 140 according to one embodiment, such as that illustrated in FIGS. 9 and 10. In the method of flow chart 280 starts with the location device 180 located proximate to or on the body of the participant 110 (person, animal, user, user device or user vehicle, generally referred herein as the participant 110). The location device 180 obtains/determines the location data 184 and transmits, communicates or otherwise provides, the location data 184 to location transceivers 176. The location data 184 is received in process 282 via location transceiver 176 and provided to location detection system 178 that can be then provided to the timing system 104 as a part of process 282. The timing system 104 stores the location data 184 in process 284 and uniquely identifies the received and stored location data 184 with a participant 110 such as by correlating with the participant tag number, by way of example. The timing system 104 determines if there is RFID tag read 114 associated with the participant 110 having the same tag number. If not, in this embodiment, the system continues to collect location data 184 until the timing system has a matching location data 184 and RFID tag read 114 in process 286. When this is achieved, the RFID tag read 114 with its tag read time is stored in memory 304 associated with the stored location data 184 for the same participant 110 in process 290. In process 292, the multiple instances of the location data 184 and tag reads 114 are retrieved by the timing system 104 and the timing utilizes these location data 184 and tag reads in process 294 for calculations such as computing or identifying the geodetic location of the participant 110 at various instances in time, including near real time, and can also compute other information such as the pace and velocity, by way of example, of the participant 110 along course 140. The processes 292 and 294 can be initiated by a request in process 298 for such data or for identification or determination of a virtual location point VLP such as a virtual split point, by way of example. After the calculations are performed in process 294, the data or information computed in process 294 is provided internally to the timing system 104 for use thereby or can be provided via an output interface in process 296 to an interfacing system such as those identified by way of example in FIG. 3 and the above related text. Process 280 can be used for the development of virtual timing points along with RFID tag reads as illustrated in the course 450 of FIG. 10. As shown, detection points 144A, 144B, 144C 144D, each having a tag reader 106 that identifies and obtains and provides tag reads 114 with tag read times. At these detection points, the participant 110 is in proximity to a location transceiver 176 and provides location data such as LPA, LPB, and LPC, respectively. Included in these location data transmissions however are a plurality of additional location data 184 that can be utilized by the timing system 104 using process 280 of FIG. 8 to develop virtual location points VLPN (shown as VLP1, VLP2, VLP3, VLP4, VLP5, and VLP6 and generally as VLP in FIG. 10.

In another embodiment, FIG. 9 illustrates use of the present system without RFID tag readers 106 for development of a virtual route 140 that is defined of virtual location points with a start at VLP1, and end at VLP7 and with split points VLP2, VLP3, VLP4, VLP5 and VLP 6 located between the start VLP1 and the finish VLP7. As shown in FIG. 9, none of the detection points are necessarily physical detection points having RFID tag readers 106, but are virtually located via the location device 180 providing a plurality of location data 184 that is received by the timing system 104 of the location detection system 178 via location detection transceivers 176. The course 140 is determined by the path 142 traveled by the participant 110 based on the captured/determined and transmitted location data 184.

FIG. 9 illustrates the use of a mobile device such as a mobile phone equipped with a location tracking device to geographically define locations for a route and to also map or identify virtual location or split points along the course according to one exemplary implementation. The event timing system 104 is communicatively coupled to RFID tag 112 for receiving tag read 114 from tag readers 106 with their antenna 108 as well as received captured images 150 from image capture devices 130. The timing system 104 also receives location data 184 as described above. The timing system 104 includes memory 304 and is communicatively coupled via a data network 320 such as a wireless network to participant registration system 1118 for receiving participant data 158, such as requests to establish one or more virtual location points VLP or participant data related thereto. The participant registration system 118 is accessed by a user or participant by using one or more user device 156 for inputting user data 158 as well as participant image 158 that can be utilized by the timing system 104 or the participant identification system 102 as described above. This can also include the identification or authorization of participant defined outputs for providing location data 184 or calculations made therefrom such as in FIG. 8 or captured images 150 associated with the particular participant 110 that can be at any detection point 144 or possibly a virtual location point VLP as identified in the user request data 158. This can include providing a captured image 150 that is identified by the system 152 at an identified location based on the location data 184 as being that of the participant 110 to a telephone number for text messaging, to a url or to an IP address such as a website or user name for a website. The outputs for the providing of a captured image 150 of a particular identified participant 110 can include an image library 220, a biometric module 200, an event or participant medical system 198, an event announcer or broadcast network 218, a kiosk or billboard 202, a web site 204, a mobile or cell phone 206, or another mobile device 208, with any of these being via an application or messaging format or system as may be desired or suitable. The system can include an encryption engine 210, a compression engine 212, a database engine 214 and a biometric data push server 216 in various embodiments and combinations thereof. This can also include creation of email messages 203, short message session SMS text messages, or updating a social network page 209 of the participant or the event, and/or creating a message to a broadcast network 201 such as a TV or Radio or similar network covering the event.

Figure 12:
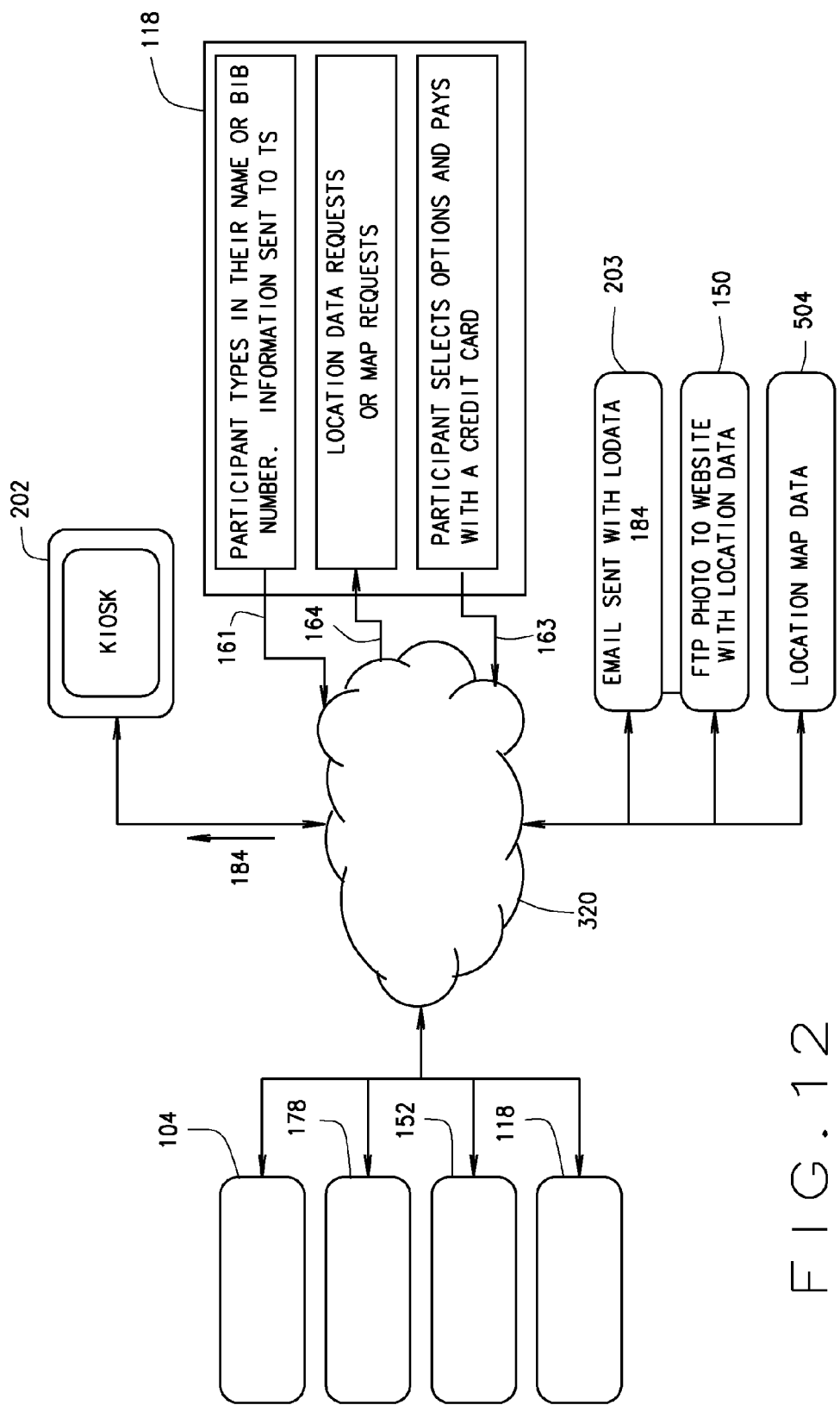
FIG. 12 is a block diagram of a system for requesting the tracking of a participant during an event using the location data and for providing the requested tracking by various delivery means.

FIG. 12 is a block diagram of a participant management system 102 having a timing system 104, a location detection system 178, an image capture system 152 and a participant registration system 118 coupled together via network 32. As such, a kiosk 202 can be provided with the location data 184 and an email 203 sent with the location data 184. This can also include updating or sending a captured image 150 to a website 204 or a social network page 209. These can also include transmitting or updating a route map location in 504 whereby the current and past locations of the participant 110 is tracked and/or displayed. The outputs and displays are determined by the user or event organizer using the participant registration system 118 for inputting the name and bib or participant number of the participant as data 161 providing a selection of location or map requests 164 for selection by the user of the system 118 and possibly having the user enter payment information 163 related to the payment of incremental charges for providing location data output via the desired or requested location data 184 output methods as an increments event management service.

Figure 13:
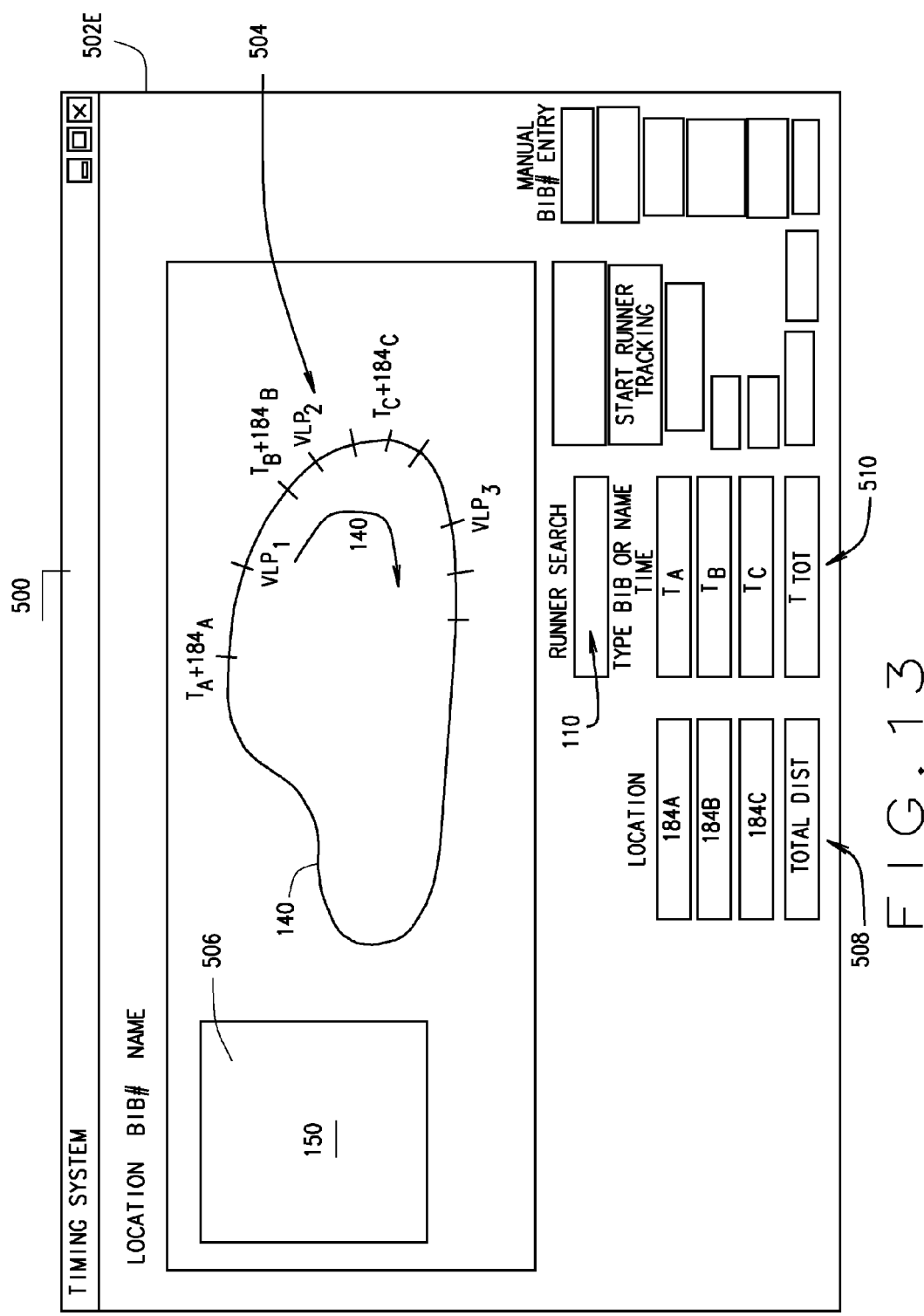
FIG. 13 is a screen shot of a course map that was mapped using location data and for which the split points are identified and that shows the tracking and status of the participant along such tracked route and statistic related thereto.
Figure 14:
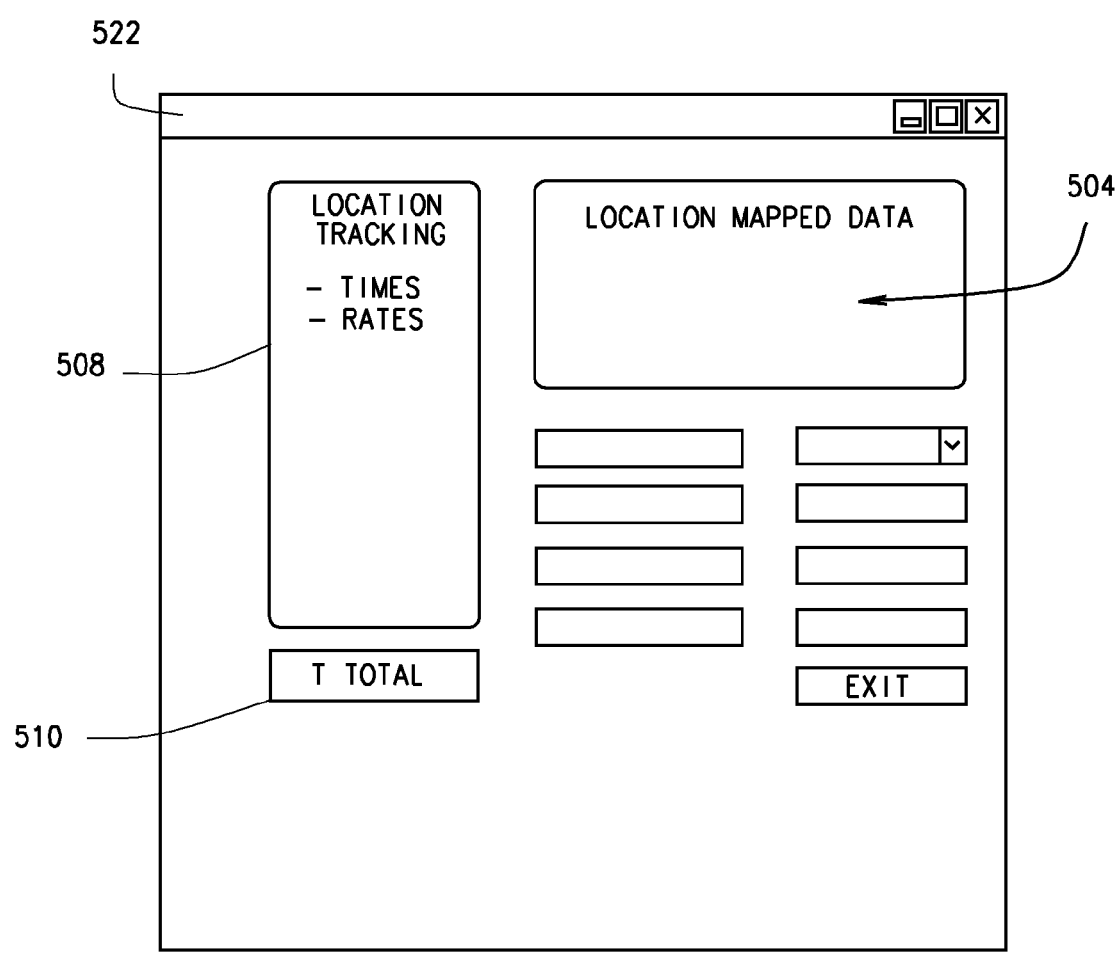
FIG. 14 is an illustration of a webpage or mobile app for providing a display of participant tracking showing a map and location tracking data and statistics determined therefrom.

FIG. 13 is a screen shot 500 of a participant management system output display 502 and FIG. 14 is a similar illustration of a mobile app 520 with mobile display 522 all of which can include displaying of participant information and data. This can include a display of a map 504 of the course 140 along with the times TA, TB, TC and tag reads 114. This can also display location data 184A, 184B and 184C at detection points DPA, DPB, and DPC as well as virtual locations points VLP of the participant 110 such as VLP1, VLP2, and VLP3, by way of example. This display can also in include a participant image display 506 showing a captured image 150 along with a listing of the location data 184A, 184B, 184C and total distance traveled for each to times TA, TB, TC and total time TTOT as shown in screen positions 508 and 510 respectively. This is just one example of a possible displayed output of the location data 184 integration with the participant management system 102 with a timing system 104 and a location detection system 178 as described by the various embodiments herein.

Exemplary Digital Processing System Environment

Figure 15:
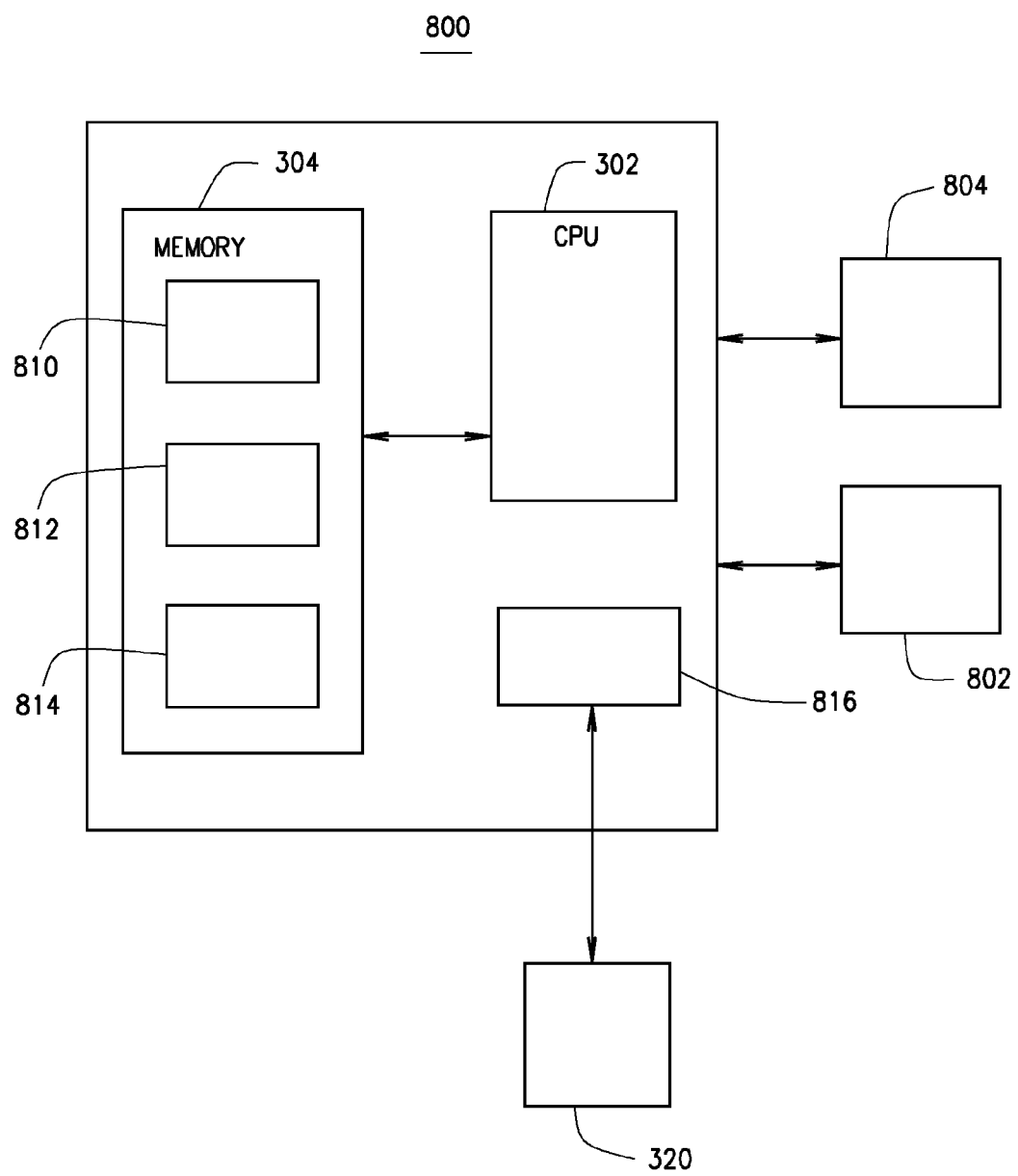
FIG. 15 illustrates an exemplary computer system environment according to one embodiment.

The systems, platforms, servers, applications, modules, programs, and methods described herein for the event participant management system 102 including the timing system 104 and the biometric module 122 among other components. Each of these can include one or more a digital processing systems 800 as shown in FIG. 15. Each component can include one or more hardware central processing units (CPU) 302 that carry out the functions as described above. The digital processing system 800 includes an operating system configured to perform executable instructions for the operation thereof. In most embodiments, the described digital processing systems 800 includes one or more memory devices 304, a display 802, one or more input devices 804, and in some embodiments can include a sound output device such as an alarm or status or verification signal. In some embodiments, the digital processing system 800 can be connected to one or more data networks 320 that can be a wired network, a mobile network, a wireless network such as a Wi-Fi or a Bluetooth™ network or a wired data network. These data networks 320 can be utilized to access the Internet or an intranet such as for accesses to the World Wide Web or other Internet based services. These can include, but are not limited to such data network accessible systems or applications such as a data storage device, a cloud service, an application server, a terminal or exchange server. In some embodiments, the digital processing system 800 is a non-portable device, such as a server or a desktop computer but in many embodiments it can be a portable device, such as a laptop, tablet computer, a mobile telephone device or a digital audio player.

The systems, platforms, servers, programs, and methods disclosed herein for one or more components or features of the system 100, the event management system 102, RFID reader 106, the timing system 104 or the biometric modules 116 and 122 can include one or more computer programs each of which are composed of sequences of computer executable instructions for the digital processing system's CPU each of which are developed to perform one or more specified tasks. Those of skill in the art will recognize that the computer program may be written in various computer programming languages having one or more sequence of instructions. The computer program can be loaded to the CPU 302 or associated memory 304 via a data network connection 320 or a local memory device, but are increasingly via a data network download. Typically, a computer program such as the operating system 810 is loaded by local memory device 304 such as CD or DVD. In some embodiments, the computer program is delivered from one location to one or more locations and can be increasingly distributed via a cloud computing or application service. In various embodiments, the computer program comprises, in part or in whole, one or more web, web browser, mobile, standalone or applications, extensions, add-ins, or add-ons, or combinations thereof. The systems, platforms, servers, programs, and methods disclosed herein above and throughout include, in various embodiments, software, server, and database modules. The software modules are created by techniques known to those of skill in the art using machines, software, and languages known to the art, some of which are disclosed above.

As noted, a digital processing system 800 typically includes one or more memory or data storage devices 304. The memory 304 stores data including the operating system 810 and application programs 812 as well as operating data 814 on a temporary or permanent basis. In some embodiments, the memory 304 can be volatile and requires power to maintain stored information but can also be non-volatile and retains stored information when the digital processing system 800 is not powered. Further, the memory 304 can be located with the digital processing systems 800 or can be attachable thereto either physically or via a data network connection to a remote memory 304. In some embodiments, the memory 304 can also include flash memory devices, solid state memory, magnetic disk drives, magnetic tape drives, optical disk drives, cloud computing systems and services, and the like.

As noted, the digital processing system 800 includes an operating system 810 configured to perform executable instructions which is stored in memory 304. The operating system can include software, including programs and data, which manages the device's hardware and provides services for execution of software applications/modules. Those of skill in the art will recognize that suitable operating systems can include, by way of non-limiting examples, Apple OS®, Microsoft® Windows®, Microsoft®, Windows®, Apple® Mac OS X®, UNIX®, and UNIX-like operating systems such as GNU/Linux®. In some embodiments, the operating system can be provided by cloud computing. Those of skill in the art will also recognize that embodiments of the remote control panel and some components of the primary control panel system may also be implemented using suitable mobile smart phones that include mobile operating systems including, by way of non-limiting examples, Nokia® Symbian®, OS, Apple® iOS®, Research In Motion® BlackBerry OS®, Google® Android®, Microsoft® Windows Phone®, OS, Microsoft® Windows Mobile®, OS, Linux®, and Palm® WebOS®.

The digital processing system 800 can include a visual display 802. In some embodiments, the display 802 can be computer controlled cathode ray tube (CRT) or an optical projector, but is increasingly a flat screen such as a liquid crystal display (LCD), a plasma display, a thin film transistor liquid crystal display (TFT-LCD), a light emitting diode (LED) or an organic light emitting diode (OLED). In other embodiments, the display 802 can also be a combination of devices such as those disclosed herein. Typically they are located proximate to one of the digital processing systems 800 but in some embodiments, the display can be remotely located such as a billboard using LED or electrowetting technology.

The digital processing system 800 can also include one or more an input devices 804 that can be a push button, a key switch, a switch, a keyboard, a touch screen or keypad but these can also include a pointing device such as, by way of non-limiting examples, a mouse, touchpad, light pen, pointing stick, trackball, track pad, joystick, game controller, stylus, multi-touch screen, a microphone that captures voice or other sound inputs or an optical image capture device that can capture images or motion or other visual input. In still further embodiments, the input device 804 can be a combination of devices such as those disclosed herein.

In some embodiments, the digital processing system 800 optionally includes one or more sound output devices (not shown but known to those of skill in the art). These sound output devices can be a set of speakers, a pair of headphones, earphones, or ear buds. The speakers can be of any technology including a flat panel loudspeaker, a ribbon magnetic loudspeaker, an electro-acoustic transducer or loudspeaker or a bending wave loudspeaker, or a piezoelectric speaker. In still further embodiments, the sound output device can be a combination of devices such as those disclosed herein.

Such systems utilize one or more communications networks 320 can include wireline communications capability, wireless communications capability, or a combination of both, at any frequencies, using any type of standard, protocol or technology. In addition, in the present invention, communications network 320 can be a private network (for example, a VPN) or a public network (for example, the Internet). A non-inclusive list of exemplary wireless protocols and technologies used by communications network 320 includes BlueTooth™, general packet radio service (GPRS), cellular digital packet data (CDPD), mobile solutions platform (MSP), multimedia messaging (MMS), wireless application protocol (WAP), code division multiple access (CDMA), short message service (SMS), wireless markup language (WML), handheld device markup language (HDML), binary runtime environment for wireless (BREW), radio access network (RAN), and packet switched core networks (PS-CN). An exemplary non-inclusive list of primarily wireline protocols and technologies used by communications network 320 includes asynchronous transfer mode (ATM), enhanced interior gateway routing protocol (EIGRP), frame relay (FR), high-level data link control (HDLC), Internet control message protocol (ICMP), interior gateway routing protocol (IGRP), internetwork packet exchange (IPX), ISDN, point-to-point protocol (PPP), transmission control protocol/internet protocol (TCP/IP), routing information protocol (RIP) and user datagram protocol (UDP). As skilled persons will recognize, any other known or anticipated wireless or wireline protocols and technologies can be used.

In accordance with the description provided herein, a suitable digital processing system 800 can include, by way of example, server computers, desktop computers, laptop computers, notebook computers, tablet computers, mobile phones such as smart phones, audio devices, personal digital assistants, netbook computers, smartbook computers, subnotebook computers, ultra-mobile PCs, handheld computers, Internet appliances, and video game systems both portable and fixed.

Figure 16:
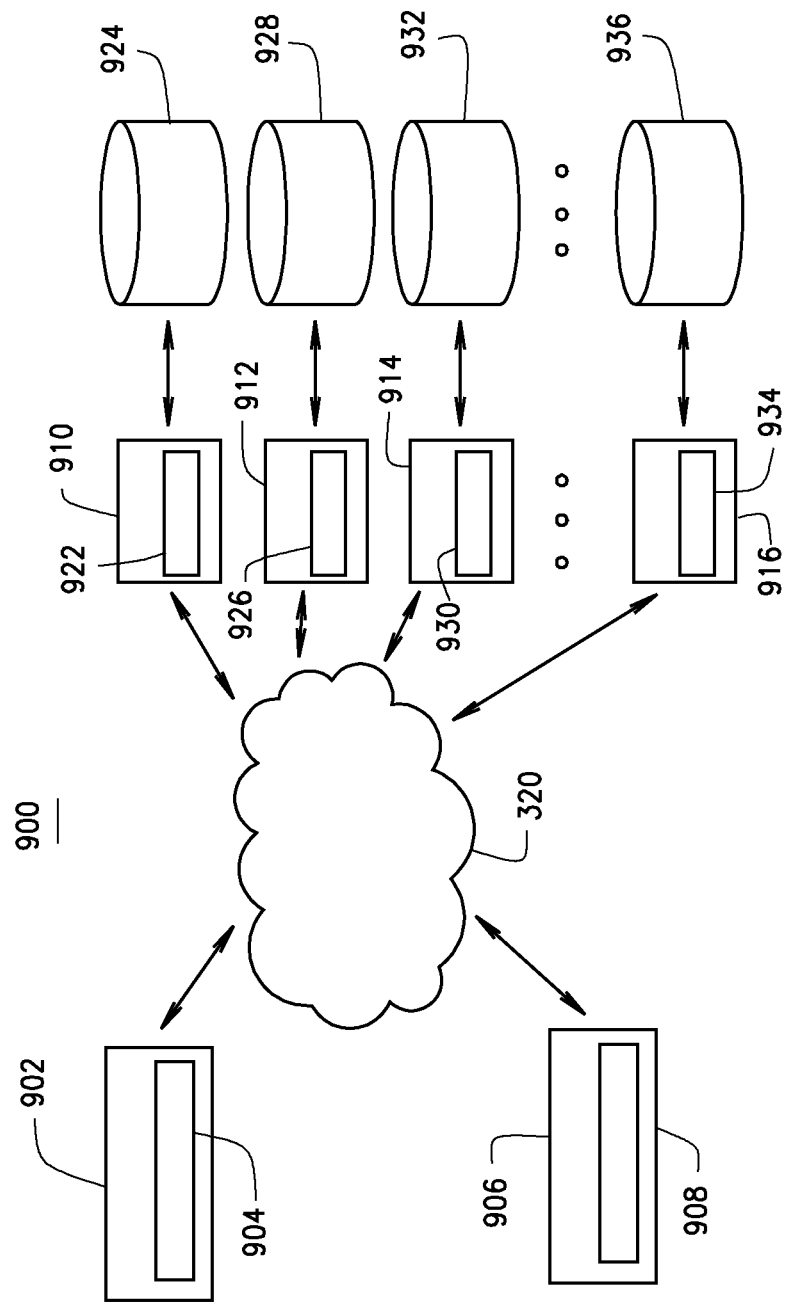
FIG. 16 illustrates an exemplary client-server environment according to yet another embodiment.

FIG. 16 illustrates a detailed exemplary client-server environment 900. Environment 900 of FIG. 16 includes the aforementioned communications network 320, a plurality of clients 902, 906 and a plurality of servers 910, 912, 914, 916 connected to network 320. The servers 910, 912, 914, 916 are shown connected to a plurality of database servers (DSs). Specifically, server 910 is connected to DS 924, server 912 is connected to DS 928, server 914 is connected to DS 932, and server 916 is connected to DS 936. As one example, the timing system 104 can be implemented as a server 914 and one or more biometric modules 122 can be implemented as a client, 902, 906.

The clients 902, 906 and the servers 910-916 are nodes connected to network 520, defined by their respective information retrieval functions. Client 902 includes a client application 904, which is an information requesting or receiving application associated with client 902, and client 906 includes a client application 908, which is an information requesting or receiving application associated with client 906. Client applications 904, 908 can run either on clients 902, 906, respectively, or can run on another node and are then passed to the clients 902, 906. In one or more embodiments, the client applications 904, 908 are web browsers.

Servers 910-916 include a variety of processes, including operating systems, web server applications and application servers. The operating systems, which can also be called platforms, are the software programs that applications use to communicate with the physical parts of the servers 910-916. Examples of operating systems that can be used with the present invention include: Linux™, Sun Solaris™, Windows NT/2000™, Cobalt RaQ™, and Free BSD™, although any operating systems known or anticipated can be used.

The web server applications are software running on servers 910-916 that make it possible for the client browsers 904, 908 to download stored web pages. These applications also coordinate streaming audio, video, and secure e-commerce, and can be integrated with databases (as described below) for information retrieval. Examples of web server applications that can be used with the present invention include: Apache™, Microsoft's Internet Information Server (IIS)™, O'Reilly & Associates WebSite Pro™, Netscape's FastTrack Server™, and StarNine's WebSTAR™ (for Macintosh), although any operating systems known or anticipated can be used.

The application servers sit on top of the formatting and display languages (for example, HTML) such that a request from clients 902, 906 is generated and translated as a request to the databases. Upon receiving information from databases, the application servers will translate this information back to the formatting and display languages and sent a response back to the browser. In one or more embodiments, the application server software resides at the servers 910-916, although with cross-platform programming technology, software performing the same functions can reside at clients 902, 906 as well. In one or more embodiments, the application servers will insert strings of programming code into the formatting and display language, with client browsers 904, 908 employing interpreters (or a plug-ins) to translate back into the formatting and display language (for example, HTML) to display a page. Examples of application servers that can be used with the present invention include: Cactus™, Cold Fusion™, Cyberprise Server™, Ejipt™, Enterprise Application Server™, Netscape Application Server™, Oracle Application Server™, PowerTier for C++™, PowerTier for Enterprise Java Beans™, Secant Extreme™, Enterprise Server™, SilverStream™, WebEnterprise™, WebSpeed™, and WebSphere™ although any application servers known or anticipated can be used.

Taken together, the web servers and applications servers perform at least these functions: (i) providing an environment upon which server components can run; (ii) functioning as is a main program under which other components run as subroutines; (iii) providing services (for example, security related services, transaction related services), state management, and resources (for example, database connections); (iv) enabling communication with clients 902, 906.

Figure 11:
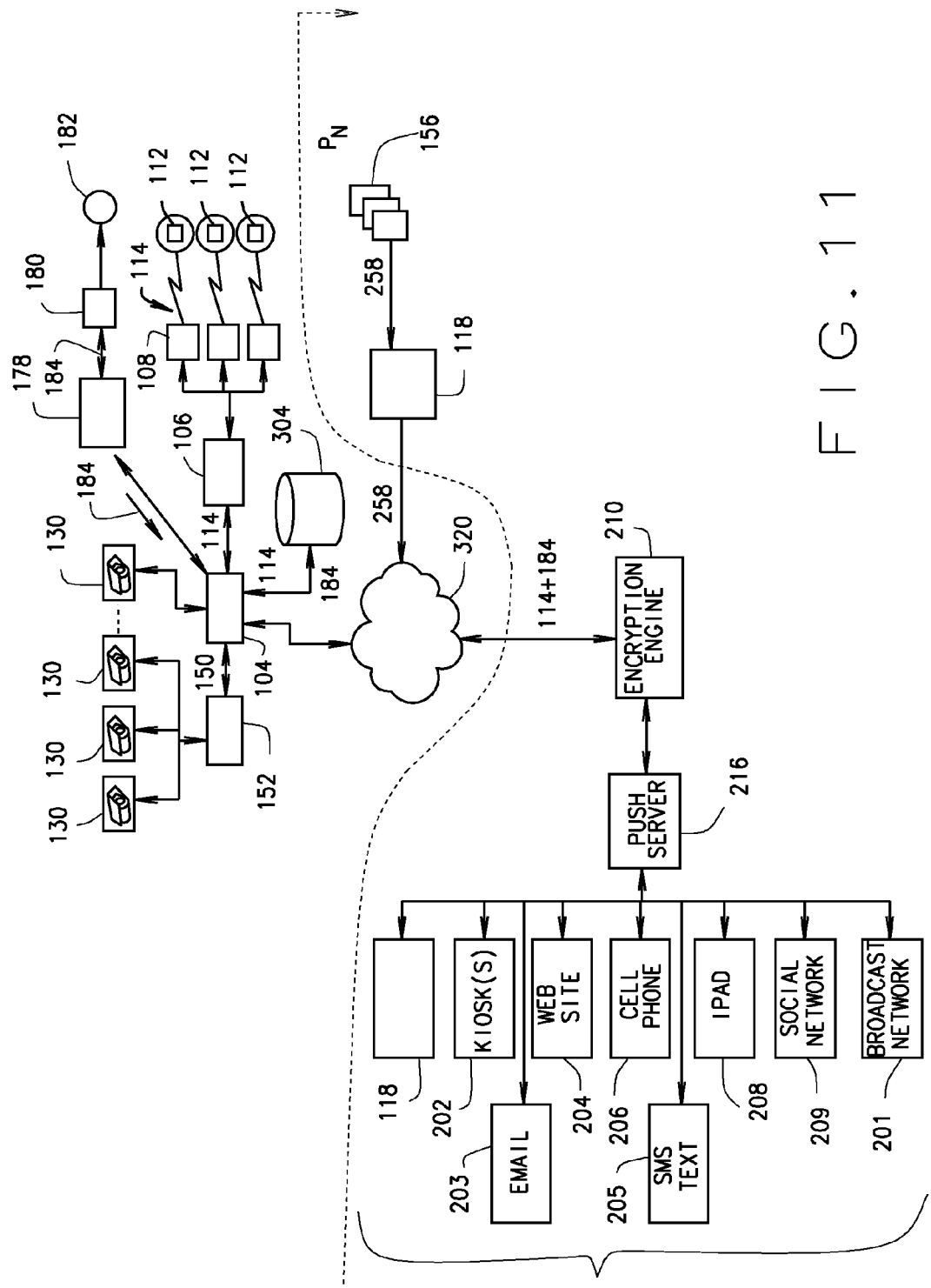
FIG. 11 is a block diagram of a timing system according to some embodiments of the present disclosure.

For the convenience of condensing terminology, the aforementioned applications working, which work together on the servers 910-916 (or instead are processed at other nodes and passed to servers 910-916) are referred to as "application servers." FIG. 11 illustrates applications servers (ASs) 922, 926, 930, 934 respectively can run on clients 910, 912, 914, 916. In operation, client browsers 904, 908 are used to issue requests for information, or queued to transmit information, over network 520. Requests and responses are handled by servers 910-916 via running of ASs 922, 926, 930, 934, which in turn transmit information over network 520 for display by browsers 904, 908.

In one or more embodiments, additional functions required of ASs 922, 926, 930, 934 will be to connect the web servers 910-916 to, for example, back-end data resources such as relational tables, flat files, e-mail messages, and directory servers. In exemplary embodiments, additional programs incorporated in ASs 922, 926, 930, 934 typically called "middleware," database utilities, or database management systems (DMBS) can be used, among other known or anticipated database methods.

For example, the ASs 922, 926, 930, 934 can include their own internal DBMSs, or DBMSs of other nodes, or the DBMSs labeled database servers (DSs) 924, 928, 932, 936. The DBMS refers to computer software for storing, maintaining, and searching for data in a database. In the present invention, the DBMS can also utilize facilities for increasing reliability and performance, and integrity, such as indexes, logging, and record locking.

In one or more embodiments, the DBMS includes interfaces for searching for and locating particular data items from the database and for presenting the result of these queries to a search engine. A search engine as used herein searches the database in response to a user request, which can be initiated at client browser 902, 906, for example, or at server 922-924, for example, and returns a result to the user, for example in the form of a relational table viewable in browsers 904, 908. The DBMS can refer to any type of database, including a relational DBMS (RDBMS), LDAP™, VSAM™, IMS™, Active Directory Services™, message stores, to name a few.

In one or more embodiments, the DBMS is an RDBMS that uses relational database to retrieve information from the timing system 104 to obtain participant data including biometric data 120. In one or more embodiments, the relational database uses structured query language (SQL™), including SQL defined according to International Standards Organization (ISO) and American National Standards Institute (ANSI) standards, or follow these standards with additional language constructs. In one or more exemplary embodiments, ASs 922-924 are respectively connected to DSs 924-936 via an application programming interface (API), including for example the open database connectivity (ODBC™), Java database connectivity (JDBC™), APIs.

Any types of DBMS platforms can be used in the various systems and components of the systems described herein and methods thereof. Exemplary platforms that can be employed include Sun Microsystems' Java™, 2 Platform, Enterprise Edition (J2EE)™ that contains an Enterprise JavaBeans™. (EJB) server-side component architecture, and Microsoft's Windows™, Distributed interNet Applications Architecture (Windows DNA™), which contains the COM+™ server-side component architecture.

As described, the presently disclosed system and method is an improved timing system that utilizes identifying of a location of the RFID tag within a coordinate system and utilizing the determined location for determining the time of passing of the participant past a monitored line that is within the same coordinate system. In this manner, the present system and method provides a more accurate determination of the actual point of passing of the participant past the monitored line than prior art RFID tag reader based timing systems.

When describing elements or features and/or embodiments thereof, the articles "a", "an", "the", and "said" are intended to mean that there are one or more of the elements or features. The terms "comprising", "including", and "having" are intended to be inclusive and mean that there may be additional elements or features beyond those specifically described.

Those skilled in the art will recognize that various changes can be made to the exemplary embodiments and implementations described above without departing from the scope of the disclosure. Accordingly, all matter contained in the above description or shown in the accompanying drawings should be interpreted as illustrative and not in a limiting sense.

It is further to be understood that the processes or steps described herein are not to be construed as necessarily requiring their performance in the particular order discussed or illustrated. It is also to be understood that additional or alternative processes or steps may be employed.

What is claimed is:

1. A system for determining a location along a route being traveled by a participant having a participant identifier that will be tracked and timed during an event, the system comprising:

an RFID tag reader transmitting a tag read request and in response receiving a tag read from an RFID tag having an RF interface transmitting an RFID tag read including the participant identifier associated with the RFID tag responsive to the tag read request, the RFID tag reader determining a time for the received tag read and identifying the participant number associated with the tag read, the tag reader transmitting a tag read message over a timing system interface with the determined tag read time and the participant number;

a location device associated with the participant and the participant identifier, the location device having a location information receiver receiving location information from a location providing source, a location determination module determining a participant location from the received location information and a wireless communication interface for transmitting the determined location as location data that includes the participant identifier;

a location determination system in at least periodic wireless communication with the wireless communication interface of the location device receiving the transmitted location data and determining a participant location from the received location data; and a timing system receiving the participant location from the location determination system, and receiving the tag read message including the tag number and tag read time from the tag reader, associating the participant location with the tag read and tag read time, the timing system determining participant position along the route as a function of the received participant location, and generating a participant location message over an output interface the tag read time and at least one of the participant location and the determined participant route position.

2. The system of claim 1 wherein at least one of the location device, the location determination system and the timing system, includes a clock and identifies and associates a time of the location data with the location data and wherein the timing system associates that location data time with the participant location and the generated participant location message includes the location data time.

3. The system of claim 1 wherein the timing system receives the location data as well the participant location.

4. The system of claim 1 wherein the timing system receives location data associated with the route as route location data having a plurality of route location points, and timing system associates the participant location with at least one of the route location points, and the generated participant location message includes the associated at least one route location point.

5. The system of claim 4 wherein the timing system includes a portion or all of the plurality of the route location points with the determined participant route position.

6. The system of claim 1 wherein the received location data of the route and the route location data having the plurality of location points is less than all of the locations along the route, and wherein the timing system collects a portion of the received plurality of received participant locations and/or location data, and generates a virtual location point of the participant within or proximate to the route.

7. The system of claim 6 wherein the virtual location point is a virtual split point and wherein the timing system determines a time of passing of the participant by the virtual split point and includes the determined time of passing the virtual split point in the generated participant location message.

8. The system of claim 1 wherein the timing system does not include any route location data or route location points and the route of the participant is undefined, wherein the timing system collects a plurality of participant locations from a plurality of received participant locations and/or location data, and generates a virtual route of the participant therefrom.

9. The system of claim 1 wherein the timing system determines at least one of a pace, a duration or a point of crossing a virtual waypoint of a participant along the route based on the received location data or the determined participant position along the route.

10. The system of claim 1 wherein the location device is configured for storing location data at intervals based on a predetermined rate.

11. The system of claim 1 wherein the location device is configured to receive a location download request, and wherein the location device transmits the location data over the wireless interface to the location determination system responsive to said received request.

12. The system of claim 1 wherein the location detection device only transmits the received location data responsive to the location device receiving a request that a transmission to the location determination system is currently available.

13. The system of claim 1, further comprising a remote system communicatively coupled to the timing system to receive the generated participant location message and includes a display for displaying the participant location on a display map of the route or a map of the actual geodetic route traveled by the participant or the current participant location.

14. The system of claim 13 wherein the remote system is a Kiosk, a website, a mobile phone, a portable computer, a tablet, a news station, a social network, or a broadcast network.

15. The system of claim 1 wherein the location device is configured for selective activation and deactivation of its location information receiver, and wherein the wireless interface is configured to receive activation and deactivation commands from the location determination system, and wherein the location determination system is configured for transmitting the activation and deactivation commands responsive to a command message received from the timing system and the timing system is configured for generating the command message.

16. The system of claim 1 wherein the location determination system is configured to transmit to the location device a location data request requesting all or a portion of the location data from the location device, and wherein the location device is configured to transmit the location data responsive to the location data request.

17. The system of claim 16 wherein the location determination system is configured to transmit a dump all data and then clear all data command to the location device, and wherein the location device is configured to transmit all of the location data and then clear a memory associated with the location device.

18. The system of claim 1, further comprising the RFID tag having the RF interface and receiving the TRID tag read request from the RFID tag reader and transmitting the RFID tag read including the participant identifier associated with the RFID tag responsive to receiving the tag read request.

19. The system of claim 1 wherein the location device is communicatively coupled with the RFID tag and wherein the location device provides the location data to the RFID tag and wherein the RID tag transmits the received location data to the location determination system or the tag reader.

20. The system of claim 1 wherein the location device is communicatively coupled with the RFID tag and wherein the RFID tag provides the location device with the participant identifier.

21. The system of claim 1 wherein the location device is communicatively coupled with the RFID tag and wherein the location device is configured to receive a location download request from the RFID tag, and wherein the location device transmits the location data over the wireless interface to the location determination system responsive to said received request from the RFID tag.

22. The system of claim 1 wherein the location detection device only transmits the received location data responsive to the location device receiving an indicator request that the location device and RFID tag are within range of tag reader.

23. The system of claim 1 wherein at least one of the timing system and the tag reader system detects the proximity of the RFID tag to the RFID tag reader and transmits a location data download command to the location determination system that in turn transmits a location data request to the location device, and wherein the location detection device transmits the location data responsive to the received location data request.

24. The system of claim 1 wherein the timing system is configured to transmit the location data associated with a particular RFID tag number responsive to a request from a remote system.

25. The system of claim 24, further comprising further comprising a remote system communicatively coupled to the timing system to generate the request to the timing system and in response receive the generated participant location message and includes a display for displaying the participant location on a display map of the route or a map of the actual geodetic route traveled by the participant or the current participant location.

26. The system of claim 24 wherein the remote system is a Kiosk, a website, a mobile phone, a PC, a tablet, a news station, or a broadcast network.

27. A system for determining a route or waypoints along a route to be or being traveled by a participant having an RFID tag that will be tracked along such route such as during an event, the system comprising:

a tag reader system receiving one or more tag reads from the RFID tag, determining a time for each tag read, identifying the tag number of the RFID tag, and transmitting a tag read message including at least a portion of the received tag reads with the tag number and the determined times and wherein the location device is associated with the RFID tag of the participant;

a location device associated with the participant having a location data receiver for receiving location data from a location providing source, and a wireless communication interface, the location detection device receiving location information from the location providing source, time stamping each received location information, and transmitting location data associated with the location device over the wireless interface; and a location determination system in at least periodic wireless communication with the location device for receiving the transmitted location data, and transmitting the received location data;

an event/timing system receiving the transmitted location data and receiving the tag read message including the tag number from the tag reader, the timing system determining a route or waypoints along a route to be or being traveled by a participant that will be tracked along such route such as during an event or tracking of the participant along the determined route and associating the location data with the RFID tag number as provided by the RFID tag reader from at least one of the tag reads from the tag associated with the location device.

* * * * *